US012385807B2

(12) United States Patent
Diolaiti et al.

(10) Patent No.: US 12,385,807 B2
(45) Date of Patent: *Aug. 12, 2025

(54) USER-INSTALLABLE PART INSTALLATION DETECTION TECHNIQUES

(71) Applicant: Intuitive Surgical Operations, Inc., Sunnyvale, CA (US)

(72) Inventors: Nicola Diolaiti, Menlo Park, CA (US); Benjamin S. Flamm, Palo Alto, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/635,735

(22) Filed: Apr. 15, 2024

(65) Prior Publication Data
US 2024/0255377 A1 Aug. 1, 2024

Related U.S. Application Data

(63) Continuation of application No. 18/135,630, filed on Apr. 17, 2023, now Pat. No. 12,000,753, which is a
(Continued)

(51) Int. Cl.
*A61B 34/35* (2016.01)
*A61B 17/29* (2006.01)
(Continued)

(52) U.S. Cl.
CPC ............. *G01M 13/00* (2013.01); *A61B 17/29* (2013.01); *A61B 34/30* (2016.02); *A61B 34/35* (2016.02);
(Continued)

(58) Field of Classification Search
CPC ............... G01M 13/00; G05B 19/0426; G05B 2219/40458; G05B 2219/50083;
(Continued)

(56) References Cited

U.S. PATENT DOCUMENTS 5,497,061 A 3/1996 Nonaka et al.
6,219,589 B1 4/2001 Faraz et al.
(Continued)

FOREIGN PATENT DOCUMENTS

CN 105052085 A 11/2015
CN 106037872 A 10/2016
(Continued)

OTHER PUBLICATIONS

Wang et al., Intuitive operation of a wheelchair mounted robotic arm for the upper limb disabled: The mouth-only approach, 2012, IEEE, p. 1733-1740 (Year: 2012).*
(Continued)

*Primary Examiner* — McDieunel Marc
(74) *Attorney, Agent, or Firm* — Foley & Lardner LLP

(57) ABSTRACT

Techniques are described for testing whether an end effector, or component thereof, is correctly or incorrectly installed to a manipulation system. A manipulation system can include a manipulator arm configured to receive an end effector having a first moveable jaw, a transducer configured to provide first effort information of the end effector as the end effector moves, and a processor configured to provide a command signal to effect a first test move of the first moveable jaw, and to provide an installation status of the of the end effector using the first effort information of the first test move.

20 Claims, 14 Drawing Sheets

Related U.S. Application Data continuation of application No. 16/640,610, filed as application No. PCT/US2018/047484 on Aug. 22, 2018, now Pat. No. 11,662,270.

(60) Provisional application No. 62/548,878, filed on Aug. 22, 2017.

(51) Int. Cl.

| | |
|---|---|
| *A61B 34/00* | (2016.01) |
| *A61B 34/30* | (2016.01) |
| *A61B 90/00* | (2016.01) |
| *B25J 15/04* | (2006.01) |
| *B25J 19/00* | (2006.01) |
| *G01M 13/00* | (2019.01) |
| *G05B 19/042* | (2006.01) |
| *G05F 1/66* | (2006.01) |
| *H02J 3/16* | (2006.01) |
| *H02J 3/18* | (2006.01) |
| *H02J 3/38* | (2006.01) |
| *A61B 17/00* | (2006.01) |
| *B25J 9/16* | (2006.01) |

(52) U.S. Cl.
CPC ............ *A61B 34/70* (2016.02); *A61B 90/06* (2016.02); *B25J 15/0466* (2013.01); *B25J 19/0095* (2013.01); *G05B 19/0426* (2013.01); *G05F 1/66* (2013.01); *H02J 3/16* (2013.01); *H02J 3/1842* (2013.01); *H02J 3/381* (2013.01); *A61B 2017/00022* (2013.01); *A61B 2017/00725* (2013.01); *A61B 2034/301* (2016.02); *A61B 2090/065* (2016.02); *A61B 2090/066* (2016.02); *A61B 2090/0808* (2016.02); *B25J 9/1692* (2013.01); *G05B 2219/40458* (2013.01); *G05B 2219/50083* (2013.01); *H02J 3/38* (2013.01); *H02J 2300/24* (2020.01); *H02J 2300/28* (2020.01); *Y02E 10/56* (2013.01); *Y02E 10/76* (2013.01); *Y02E 40/10* (2013.01); *Y02E 40/20* (2013.01); *Y02E 40/30* (2013.01)

(58) Field of Classification Search
CPC ......... A61B 34/35; A61B 17/29; A61B 90/06; A61B 34/37; A61B 34/30; A61B 34/70; A61B 2090/064; A61B 2090/065; A61B 2017/00477; A61B 2090/066; A61B 2017/00022; A61B 2090/0808; A61B 2017/00725; A61B 2034/301; B25J 15/02; B25J 15/0466; B25J 19/0095; B25J 9/1689; B25J 9/1692; H02J 3/16; H02J 3/1842; H02J 3/381; H02J 2300/24; H02J 2300/28; H02J 3/38; G05F 1/66; Y02E 40/10; Y02E 40/30; Y02E 40/20; Y02E 10/56; Y02E 10/76

See application file for complete search history.

(56) References Cited

U.S. PATENT DOCUMENTS

| | | |
|---|---|---|
| 6,587,750 B2 | 7/2003 | Gerbi et al. |
| 6,684,129 B2 | 1/2004 | Salisbury et al. |
| 6,728,599 B2 | 4/2004 | Wang et al. |
| 6,839,612 B2 | 1/2005 | Sanchez et al. |
| 6,999,852 B2 | 2/2006 | Green |
| 7,155,316 B2 | 12/2006 | Sutherland et al. |
| 7,222,000 B2 | 5/2007 | Wang et al. |
| 7,379,790 B2 | 5/2008 | Toth et al. |
| 7,386,365 B2 | 6/2008 | Nixon |
| 8,452,447 B2 | 5/2013 | Nixon |
| 8,761,930 B2 | 6/2014 | Nixon |
| 9,085,083 B2 | 7/2015 | Nixon |
| 9,317,651 B2 | 4/2016 | Nixon |
| 9,623,563 B2 | 4/2017 | Nixon et al. |
| 9,999,476 B2 * | 6/2018 | Griffiths ................. A61B 34/74 |
| 10,258,425 B2 | 4/2019 | Mustufa et al. |
| 10,285,764 B2 * | 5/2019 | Griffiths ................. A61B 34/30 |
| 10,357,320 B2 | 7/2019 | Beira |
| 10,507,066 B2 | 12/2019 | DiMaio et al. |
| 10,603,127 B2 | 3/2020 | Hasser et al. |
| 11,197,731 B2 | 12/2021 | Hoffman et al. |
| 11,399,909 B2 | 8/2022 | Hasser et al. |
| 11,662,270 B2 | 5/2023 | Diolaiti et al. |
| 12,000,753 B2 * | 6/2024 | Diolaiti ................. A61B 17/29 |
| 2009/0088774 A1 | 4/2009 | Swarup et al. |
| 2013/0105552 A1 | 5/2013 | Weir et al. |
| 2015/0120041 A1 | 4/2015 | Wise et al. |
| 2016/0175060 A1 | 6/2016 | Park |
| 2017/0112580 A1 * | 4/2017 | Griffiths ............... F16M 13/022 |
| 2017/0172674 A1 | 6/2017 | Hanuschik et al. |
| 2017/0190050 A1 | 7/2017 | Cookson et al. |
| 2023/0251163 A1 | 8/2023 | Diolaiti |

FOREIGN PATENT DOCUMENTS

| | | | |
|---|---|---|---|
| EP | 1897511 | A2 | 3/2008 |
| EP | 2756825 | A1 | 7/2014 |
| KR | 101501529 | B1 | 3/2015 |
| KR | 20170061462 | A | 6/2017 |
| KR | 102369439 | B1 | 3/2022 |
| WO | WO-2006124390 | A2 | 11/2006 |
| WO | WO-2013063523 | A1 | 5/2013 |
| WO | WO-2013181507 | A1 | 12/2013 |
| WO | WO-2015010788 | A1 | 1/2015 |
| WO | WO-2016205162 | A1 | 12/2016 |

OTHER PUBLICATIONS

Yeotikar et al., Automation of end effector guidance of robotic arm for dental implantation using computer vision, 2016, IEEE, p. 84-89 (Year: 2016).*

Bannat et al., Artificial Cognition in Production Systems, 2011, IEEE, p. 148-174 (Year: 2011).*

Ruokangas et al., Integration of multiple sensors to provide flexible control strategies, 1986, IEEE, p. 1947-1953 (Year: 1986).*

Extended European Search Report for Application No. EP18849114.6 mailed on Jul. 30, 2020, 9 pages.

Extended European Search Report for Application No. EP23201409.2, mailed on Oct. 26, 2023, 10 pages.

Hamel., et al., "Large Scale Multi-fingered End-effector Teleportation," IEEE, 2019, pp. 3304-3310.

Hassan T., et al., "Al-Zahrawi: A Telesurgical Robotic System for Minimal Invasive Surgery," IEEE Systems Journal, Sep. 2016, vol. 10(3), pp. 1035-1045.

International Search Report and Written Opinion for Application No. PCT/US2018/047484, mailed on Mar. 5, 2019, 12 pages (ISRG08820/PCT).

Mack M.J., "Minimally Invasive and Robotic Surgery," Opportunities for Medical Research, Feb. 2001, vol. 285 (5), pp. 568-572.

McCain H.G., et al., "A Hierarchically Controlled, Sensory Interactive Robot in the Automated Manufacturing Research Facility," Proceedings. 1985 IEEE International Conference on Robotics and Automation, Jan. 2003, pp. 931-939.

Satopaa, V., et al., "Finding a Kneedle in a Haystack: Detecting Knee Points in System Behavior," 31st International Conference on Distributed Computing Systems Workshops, Jul. 2011, 6 pages.

Technology & Business, Robotics Telesurgery, 2000, Internet, 02 pages (Year: 2000).

Thomas, C and Sheldon, B., "The "Knee of a Curve"—Useful Clue but Incomplete Support," Military Operations Research, 1999, vol. 4 (2), pp. 17-24.

Tognarelli S., et al., "An Endoluminal Robotic Platform for Minimally Invasive Surgery," IEEE, Jun. 2012, p. 7-12.

(56) References Cited

OTHER PUBLICATIONS

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

USER-INSTALLABLE PART INSTALLATION DETECTION TECHNIQUES

CROSS-REFERENCE TO RELATED APPLICATIONS

This application is a continuation of and claims the benefit of priority of U.S. patent application Ser. No. 18/135,630, filed on Aug. 17, 2023, which is a continuation of and claims the benefit of priority U.S. patent application Ser. No. 16/640,610, filed on Feb. 20, 2020, which is a U.S. National Stage Filing under 35 U.S.C. 371 from International Application No. PCT/US2018/047484, filed on Aug. 22, 2018, and published as WO 2019/040598 A2 on Feb. 28, 2019, which claims the benefit of priority to U.S. Provisional Patent Application Ser. No. 62/548,878, filed Aug. 22, 2017, each of which is incorporated herein by reference in its entirety.

BACKGROUND

Robotic techniques allow a user to manipulate object via an intervening robotic system. In certain applications, the manipulation locations can be hazardous, the manipulation procedures can only be accomplished by a particular expert, such as a surgeon, for example, or the robotic technique can allow for rendition and conversion of a small manipulation environment to a virtually larger environment thus allowing for clearer vision and finer resolution of the manipulation axes to the user. In some manipulation environments or procedures, an improperly installed, or incorrectly installed, tool can raise the potential for incorrect manipulation, damage to an object within the manipulation site, or can delay or impede procedures.

OVERVIEW

Techniques are described for testing whether an end effector, or component thereof, is correctly or incorrectly installed to a manipulation system. In an example, a manipulation system can include a manipulator arm configured to receive an end effector having first moveable jaw, a transducer configured to provide first effort information of the end effector as the end effector moves, and a processor configured to provide a command signal to effect a first test move of the first moveable jaw, and to provide an installation status of the of the end effector using the first effort information of the first test move.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
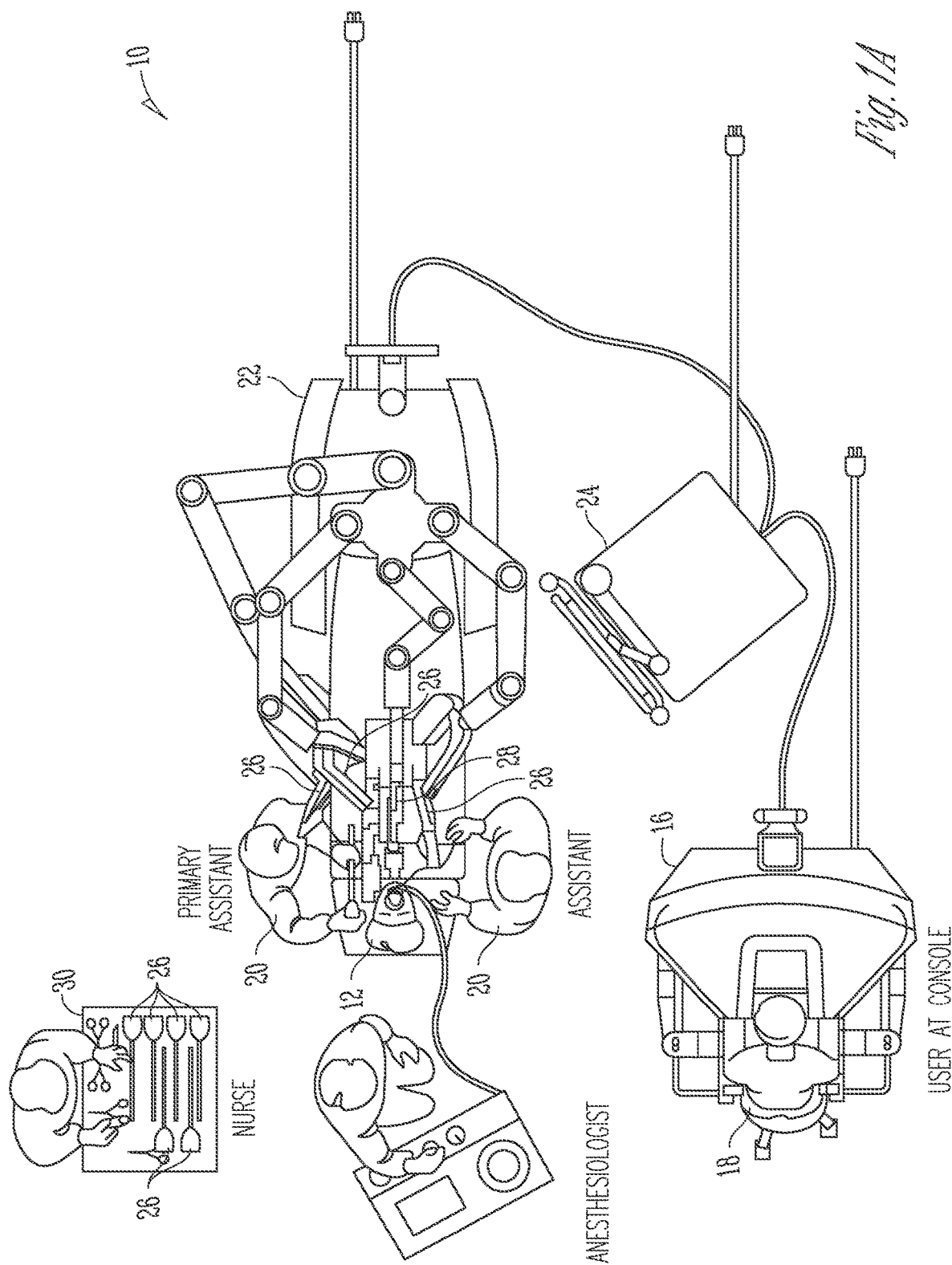
FIG. 1A illustrates generally an overhead view of an example manipulation system.

Manipulation systems including robotic arm assemblies are being developed to increase a user's dexterity while interfacing with a high precision environment as well as to allow a user to manipulate the environment from proximate to the environment or from a remote location. In some manipulation systems, the user is provided with an image of the manipulation environment at the remote location. While viewing typically a three-dimensional image of the manipulation environment on a suitable viewer or display, the user performs the manipulation procedures by manipulating the tools or manipulators holding the tools, or by interacting with master control input devices that control the motion of robotic instruments (also called "robotic tools").

Telemanipulation is a general term for systems where the user uses some form of remote control, e.g., a servomechanism, or the like, to manipulate end effector instrument movements rather than directly holding and moving the instruments by hand.

Robotic arm assemblies can be operated to control motion of instruments in a workspace. For example, such robotic manipulators can be used to perform non-medical and medical procedures. As a specific example, teleoperated surgical manipulators can be used to perform minimally invasive medical techniques.

In telesurgery or telemedicine, a form of a telerobotics or telemanipulation, the robotic instruments can be inserted through small, minimally invasive surgical apertures or natural orifices to treat tissues at surgical sites within the patient, to obtain images or tissue for biopsies, and the like. These robotic systems can move the working ends of the instruments with sufficient dexterity to perform quite intricate tasks, often by pivoting shafts of the instruments at the minimally invasive aperture, sliding of the shaft axially through the aperture, rotating of the shaft within the aperture, and/or the like.

Although some of the examples described herein often refer to medical procedures and medical instruments, the techniques disclosed also apply to non-medical procedures and non-medical instruments. For example, the instruments, systems, and methods described herein may be used for non-medical purposes including industrial uses, general robotic uses, and/or detection or manipulation of non-tissue work pieces. Other example applications include imaging of human or animal anatomy, gathering data from human or animal anatomy, setting up or taking down the system, training medical or non-medical personnel, and/or cosmetic improvements to humans, animals, or inanimate objects. Other example applications include use for procedures on tissue removed from human or animal anatomies (without return to a human or animal anatomy), or for procedures on human or animal cadavers. Further, these techniques can also be used for medical treatment or diagnosis procedures that includes, or does not include, surgical aspects.

Similarly, although some of the examples described herein refer to teleoperated systems or procedures, the techniques disclosed also apply to non-teleoperated systems and procedures.

A variety of structural arrangements can be used to support the robotic instruments at the manipulation environment. The driven linkage or "slave" is often called a robotic manipulator, and example linkage arrangements for use as a robotic manipulator during for example, minimally invasive robotic surgery, are described in U.S. Pat. Nos. 6,758,843; 6,246,200; and 5,800,423, the full disclosures of which are incorporated herein by reference. The linkages described in these patents often make use of a parallelogram arrangement to hold an instrument having a shaft. Such a manipulator structure can constrain movement of the instrument so that the instrument shaft pivots about a remote center of spherical rotation positioned in space along the length of the rigid shaft. Some alternative manipulator structures are described, for example, in U.S. Pat. Nos. 6,702,805; 6,676,669; 5,855,583; 5,808,665; 5,445,166; and 5,184,601, the full disclosures of which are incorporated herein by reference.

In a medical context, aligning this center of rotation with the incision point to the internal surgical site can improve performance of the medical procedure. For example, aligning the center of rotation with a portion of a trocar or cannula or instrument at an abdominal wall during minimally invasive surgery, an end effector of the instrument can be positioned without imposing excessive forces against the abdominal wall or on the instrument shaft.

In certain forms, the robotic instrument can include an end effector such as, but not limited to, clamps, graspers, scissors, staplers, suction devices, irrigation devices, hooks, energy instruments such as electrocautery or RF based instruments, imaging devices, drills, saws, needles, and needle holders, for example. In some embodiments, the end effectors can be easily removed and interchanged with other end effectors. In some embodiments, the end effectors or can include components that can be easily be removed and replaced, such as physically protective covers, including sleeves, for example. Proper installation of the end effector or removable components of the end effector can assist a user in more efficient and successful use of a manipulation system.

The present inventors have recognized improved techniques to ensure proper installation of end effectors of manipulation system, or removable or adjustable components of an end effector of a manipulation system. The techniques can be advantageous for use with robotic systems in which a plurality of tools (also "instruments") will be mounted on and moved by an associated plurality of robotic manipulators during a procedure. The robotic systems, in some embodiments, comprise telerobotic, telemanipulation, and/or telepresence systems that include processors configured as master-slave controllers. By providing robotic systems employing processors appropriately configured to move manipulator assemblies with articulated linkages having relatively large numbers of degrees of freedom, the motion of the linkages can be tailored for work at a manipulation site. The large number of degrees of freedom allows a system operator, or an assistant, to reconfigure the manipulator assemblies while maintaining the desired end effector state, optionally in preparation for a procedure or while another use maneuvers the end effector during a procedure.

The robotic manipulator assemblies described herein will often include a robotic manipulator and a tool mounted thereon (the tool often comprising a surgical instrument in surgical versions), However, the term "robotic manipulator assembly" or "manipulator assembly" will also encompass the manipulator without the tool mounted thereon. The term "tool" encompasses both general or industrial robotic tools and specialized robotic surgical instruments, with these later structures often including an end effector that is suitable for manipulation of tissue, treatment of tissue, imaging of tissue, or the like. The tool/manipulator interface will often be a quick disconnect tool holder or coupling, allowing rapid removal and replacement of the tool with an alternate tool. The manipulator assembly will often have a base which is fixed in space during at least a portion of a robotic procedure, and the manipulator assembly may include a number of degrees of freedom between the base and an end effector of the tool. Actuation of the end effector (such as opening or closing of the jaws of a gripping device, energizing an electrosurgical paddle, or the like) will often be separate from, and in addition to, these manipulator assembly degrees of freedom.

The end effector will typically move in the workspace with between two and six degrees of freedom. As used herein, the term "pose" encompasses both location and orientation. Hence, a change in a pose of an end effector (for example) may involve a translation of the end effector from a first location to a second location, a rotation of the end effector from a first orientation to a second orientation, or a combination of both.

When used for minimally invasive robotic surgery or other medical or non-medical applications, movement of the manipulator assembly may be controlled by a processor of the system so that a shaft or intermediate portion of the tool or instrument is constrained to a limited amount of motion through an access site or other aperture. Such motion may include, for example, axial insertion of the shaft through the aperture site into a workspace, rotation of the shaft about its axis, and pivotal motion of the shaft about a pivot point adjacent the access site.

Many of the example manipulator assemblies described herein have more degrees of freedom than are needed to position and orient and move an end effector within a surgical site. For example, a surgical end effector that can be positioned and oriented with six degrees of freedom at an internal surgical site through a minimally invasive aperture may in some embodiments have nine degrees of freedom (six end effector degrees of freedom-three for location, and three for orientation-plus three degrees of freedom to comply with the access site constraints), but may have ten or more degrees of freedom. Redundant degree of freedom manipulator assemblies having more degrees of freedom than are needed for a given end effector position can be described as having or providing sufficient degrees of freedom to allow a range of joint states for an end effector position in a workspace. For example, for a given end effector position, the manipulator assembly may occupy (and be driven between) any of a range of alternative manipulator linkage positions. Similarly, for a given end effector velocity vector, the manipulator assembly may have a range of differing joint movement speeds for the various joints of the manipulator assembly within the null-space of the Jacobian.

The term "state" of a joint or the like will often herein refer to the control variables associated with the joint. For example, the state of an angular joint can refer to the angle defined by that joint within its range of motion, and/or to the angular velocity of the joint. Similarly, the state of an axial or prismatic joint may refer to the joint's axial position, and/or to its axial velocity. While many of the controllers described herein comprise velocity controllers, they often also have some position control aspects. Alternative embodiments may rely primarily or entirely on position controllers, acceleration controllers, or the like. Many aspects of control system that can be used in such devices are more fully described in U.S. Pat. No. 6,699,177, the full disclosure of which is incorporated herein by reference. Hence, so long as the movements described are based on the associated calculations, the calculations of movements of the joints and movements of an end effector described herein may be made by using a position control algorithm, a velocity control algorithm, a combination of both, and/or the like.

In certain embodiments, the tool of an example manipulator arm pivots about a pivot point adjacent an aperture. The system may utilize a hardware remote center, such as the remote center kinematics described in U.S. Pat. No. 6,786,896, the contents of which are incorporated herein in their entirety. Such systems may utilize a double parallelogram linkage which constrains movement of the linkages such that the shaft of the instrument supported by the manipulator pivots about a remote center point. Alternative mechanically constrained remote center linkage systems are known and/or may be developed in the future. Surprisingly, work in connection with the present invention indicates that remote center linkage systems may benefit from highly configurable kinematic architectures. In particular when a surgical robotic system has a linkage that allows pivotal motion about two axes intersecting at or near a minimally invasive surgical access site, the spherical pivotal motion may encompass the full extent of a desired range of motion within the patient, but may still suffer from avoidable deficiencies (such as being poorly conditioned, being susceptible to arm-to-arm or arm-to-patient contact outside the patient, and/or the like). At first, adding one or more additional degrees of freedom that are also mechanically constrained to pivotal motion at or near the access site may appear to offer few or any improvements in the range of motion. Nonetheless, such joints can provide significant advantages by allowing the overall system to be configured in or driven toward a collision-inhibiting pose, by further extending the range of motion for other surgical procedures, and the like. In some embodiments, the system may utilize software to achieve a remote center, such as described in U.S. Pat. No. 8,004,229, the entire contents of which are incorporated herein by reference. In a system having a software remote center, the processor calculates movement of the joints so as to pivot an intermediate portion of the instrument shaft about a pivot point determined, as opposed to a mechanical constraint. By having the capability to compute software pivot points, different modes characterized by the compliance or stiffness of the system can be selectively implemented. More particularly, different system modes over a range of pivot points/centers (e.g., moveable pivot points, passive pivot points, fixed/rigid pivot point, soft pivot points) can be implemented as desired.

As discussed above, some end effectors can be easily replaceable or can include adjustable or removable components. The present subject matter provides techniques for the telemanipulation system to self-check that a replaceable, adjustable or removable component is properly installed before the user is allowed to operate the end effector. In examples of telesurgery, the techniques can prevent operation of a recently replaced, adjusted or removed end effector, or component thereof from entering the surgical environment until the self-check has been completed. In certain examples, the present techniques can allow an assistant to a qualified user, such as a physician's assistant, to quickly and easily verify proper replacement adjustment or removal of an end effector or a component thereof.

FIG. 1A illustrates generally an overhead view of an example tele-manipulation system and more specifically an example Minimally Invasive Robotic Surgical (MIRS) system 10 for use in performing a minimally invasive diagnostic or surgical procedure on a patient 12 who is lying down on an operating table 14. Although the present subject matter s discussed relative to a surgical system 10, the subject matter is not so limited; the subject matter is also applicable to medical systems that do not involve surgery, and to non-medical systems such as industrial or general robotic systems. The system 10 can include a user console 16 for use by a surgeon 18 (or other operator) during the procedure. One or more assistants 20 may also participate in the procedure. The MIRS system 10 can further include a robotic manipulator assembly and an auxiliary support system. In the example shown in FIG. 1A, the robotic manipulator assembly is configured as a cart that is used patient-side during an operation, so is termed a side cart 22; meanwhile, the auxiliary support system is also configured as a cart and is called an electronics cart 24 for convenience. The side cart 22 can manipulate at least one removably coupled tool assembly 26 (hereinafter simply referred to as a "tool") through a minimally invasive incision in the body of the patient 12 while the user, or surgeon, 18 views the surgical site through the console 16. An image of the surgical site can be obtained by an imaging device 28, such as a monoscopic or stereoscopic endoscope, which can be manipulated by the side cart 22 so as to orient the imaging device 28. The electronics cart 24 can be used to process the images of the surgical site for subsequent display to the surgeon 18 through the user console 16. The number of tools 26 used at one time will generally depend on the diagnostic or surgical procedure and the space constraints within the operating room among other factors. If it is necessary to change one or more of the tools 26 being used during a procedure, an assistant 20 may remove the tool 26 from the side cart 22, and replace it with another tool 26 from a tray 30 in the operating room.

Figure 1B:
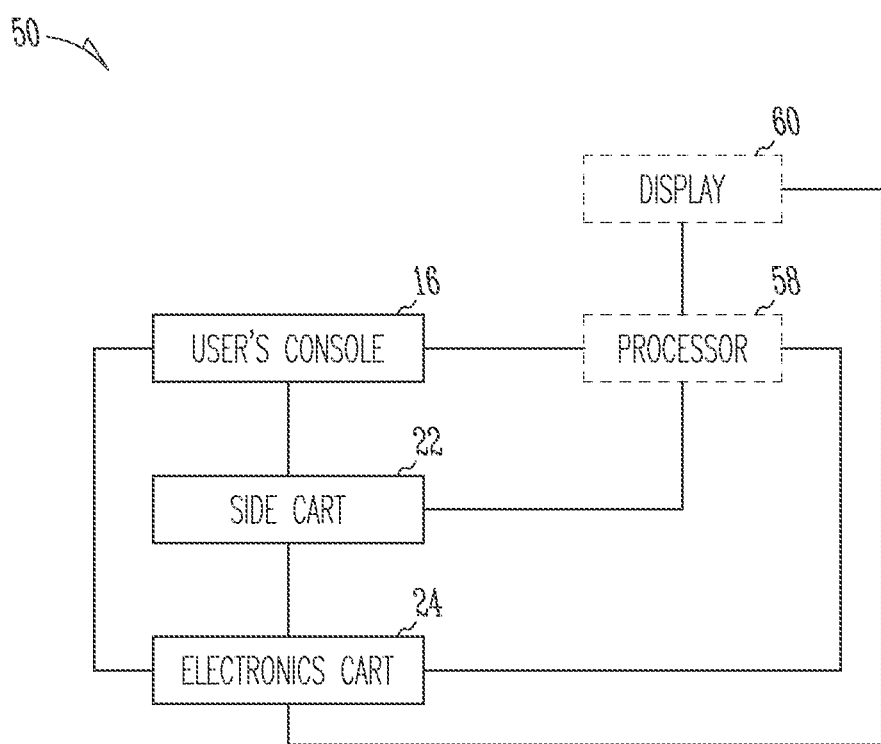
FIG. 1B diagrammatically illustrates generally an example manipulation system.

FIG. 1B diagrammatically illustrates generally an example manipulation system 50 (such as the MIRS system 10 of FIG. 1A). As applied to the MIRS system 10 of FIG. 1A and discussed above, a user console 16 can be used by a user or surgeon to control a side cart 22 during a manipulation or minimally invasive procedure. The side cart 22 can use an imaging device, such as a stereoscopic endoscope, to capture images of the procedure site and output the captured images to an electronics cart 24. The electronics cart 24 can process the captured images in a variety of ways prior to any subsequent display. For example, the electronics cart 24 can overlay the captured images with a virtual control interface prior to displaying the combined images to the user or surgeon via the user console 16. The side cart 22 can output the captured images for processing outside the electronics cart 24. For example, the side cart 22 can output the captured images to a processor 58, which can be used to process the captured images. The images can also be processed by a combination the electronics cart 24 and the processor 58, which can be coupled together so as to process the captured images jointly, sequentially, and/or combinations thereof. One or more separate displays 60 can also be coupled with the processor 58 and/or the electronics cart 24 for local and/or remote display of images, such as images of the procedure site, or other related images.

Figure 2:
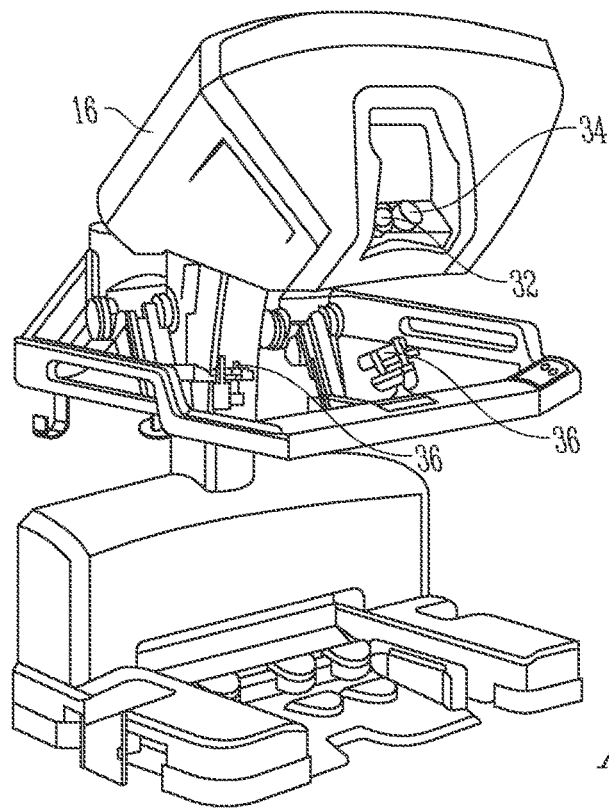
FIG. 2 is a perspective view of an example user console.

FIG. 2 is a perspective view of an example user console 16. The user console 16 can include a left eye display 32 and a right eye display 34 for presenting the user with a coordinated stereo view of the manipulation site that enables depth perception. The user console 16 can further include one or more input control devices 36 (also "input devices 36"), which in turn can cause the side cart to move one or more tools. The input control devices 36 can provide the same degrees of freedom as their associated tools so as to provide the user, or surgeon, with telepresence, or the perception that the input control devices 36 are integral with the tools so that the user has a sense of directly controlling the tools. To this end, position, force, and tactile feedback sensors (not shown) can be employed to transmit position, force, and tactile sensations from the tools back to the user's hands through the input control devices 36.

In certain situations, the user console 16 can be located in the same room as the manipulation environment so that the user may directly monitor the procedure, be physically present if necessary, and speak to an assistant directly rather than over the telephone or other communication medium. However, in other situations, the user can be located in a different room, a completely different building, or other remote location from the manipulation environment allowing for remote procedures.

Figure 3:
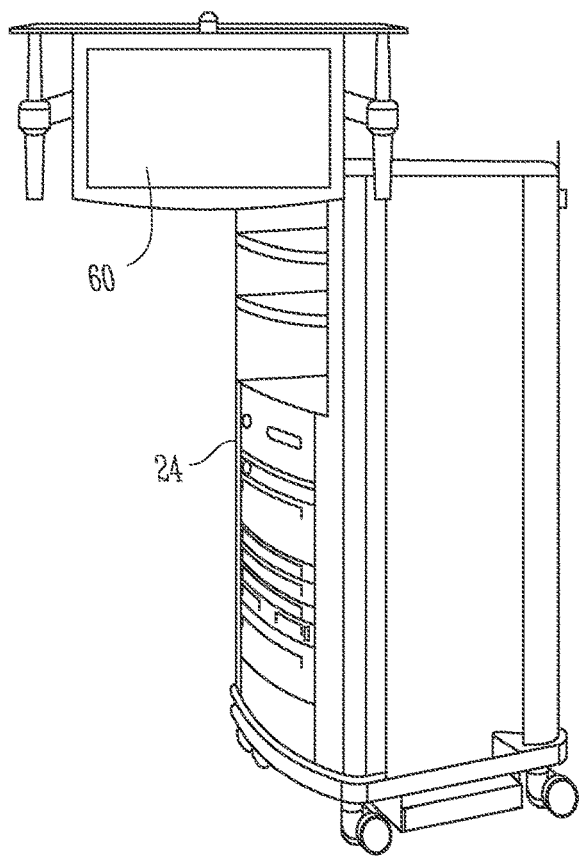
FIG. 3 is a perspective view of an example electronics cart.

FIG. 3 is a perspective view of an example electronics cart 24. The electronics cart 24 can be coupled with an imaging device 28 and can include a processor to process captured images for subsequent display, such as to a surgeon on the user console, or on another suitable display located locally and/or remotely. For example, where a stereoscopic endoscope is used, the electronics cart 24 can process the captured images so as to present the surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image capture device, such as optical aberrations.

Figure 4:
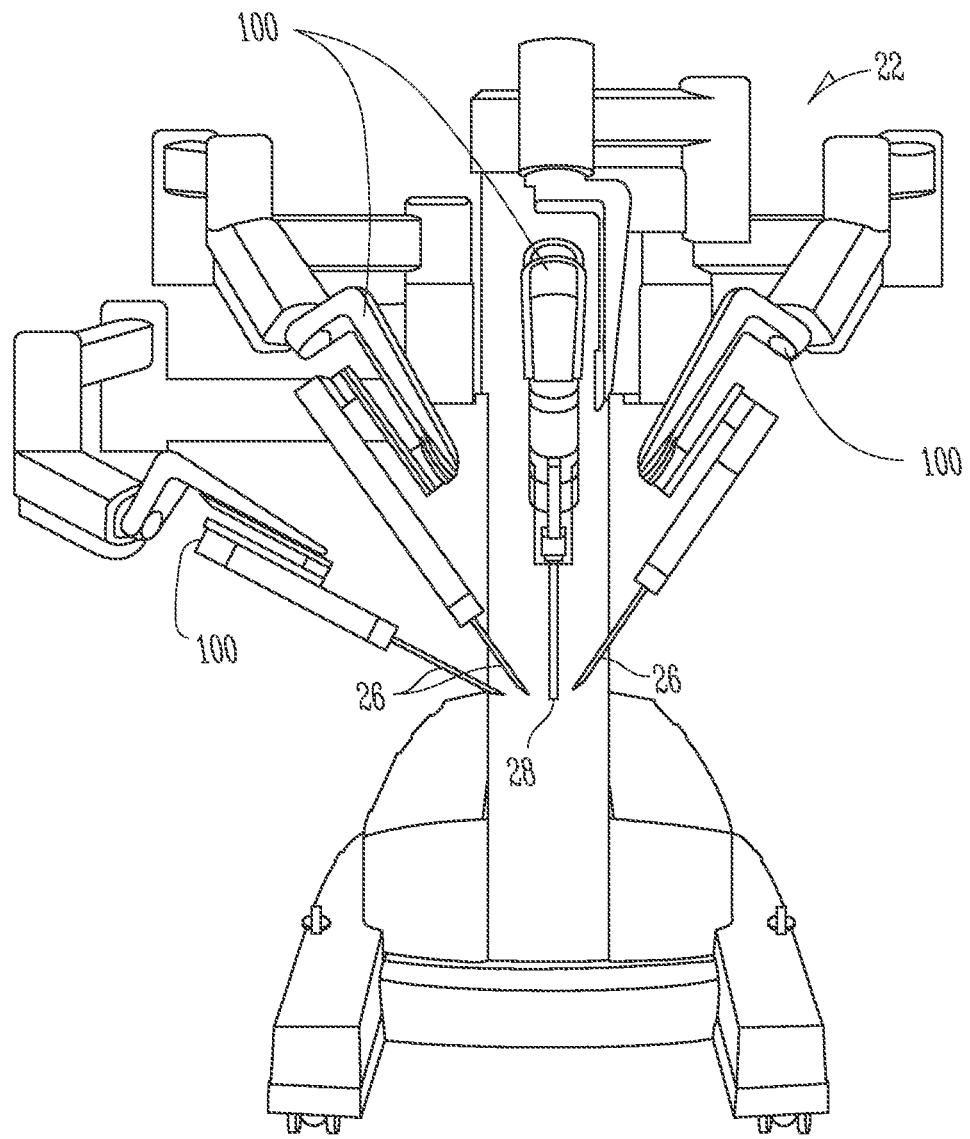
FIG. 4 illustrates generally an example robotic arm assembly having a plurality of manipulator arms, each supporting a tool at a distal portion of the manipulator arm.

FIG. 4 illustrates generally an example side cart 22 having a plurality of manipulator arms 100, each supporting a surgical instrument or tool 26 at a distal end of the manipulator arm 100. The side cart 22 shown includes four manipulator arms 100, or manipulator axes, which can be used to support either a surgical tool 26 or an imaging device 28, such as a stereoscopic endoscope used for the capture of images at the site of the procedure. Manipulation is provided by the robotic manipulator arms 100 having a number of robotic joints. For surgical applications, images of the surgical site can include images of the distal ends of the surgical instruments or tools 26 when they are positioned within the field-of-view of the imaging device 28.

Regarding tool 26, a variety of alternative robotic tools or instruments of different types and differing end effectors may be used, with the instruments of at least some of the manipulators being removed and replaced during a procedure. Several of these end effectors, including DeBakey Forceps, microforceps, Potts scissors, and clip applier include one or more end effector elements which pivot so as to define an end effector jaw or a pair of end effector jaws. Other end effectors, including scalpel and electrocautery probe have a single end effector element that may or may not pivot. For instruments having an end effector jaw(s), the jaw(s) can be closed by squeezing the grip members of a handle, and can be opened by releasing a squeezed grip member, or vice versa. Single end effector instruments may also be actuated by gripping of a grip member. In some examples, griping one of the grip member may energize, either electrically or thermally, an element of the end effector. Such examples may include, but are not limited to, an electrocautery probe or other probe that can be electrified, heated, cooled or combinations thereof.

Figure 5A:
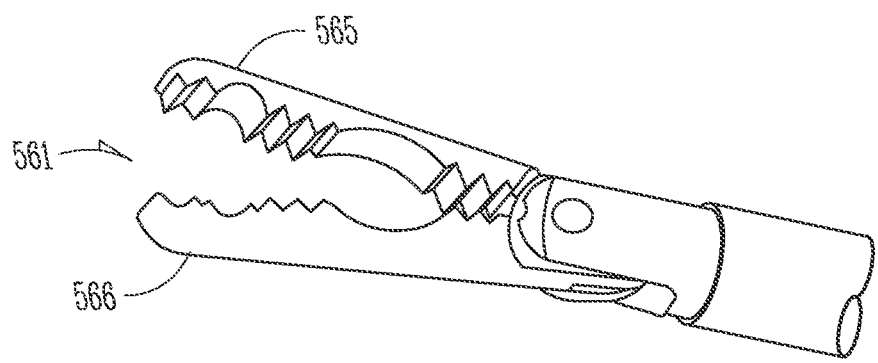
FIGS. 5A-5E, illustrate a variety of alternative robotic tools of differing types and having differing end effectors.
Figure 5B:
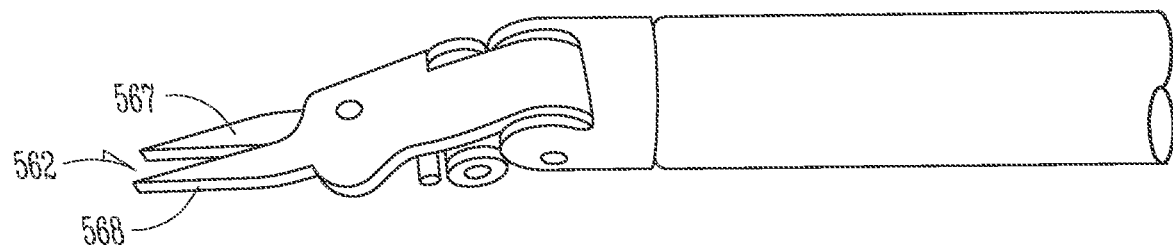
Figure 5C:
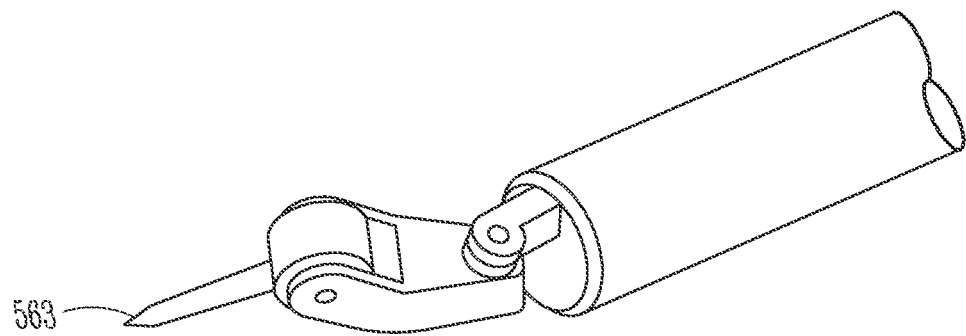
Figure 5D:
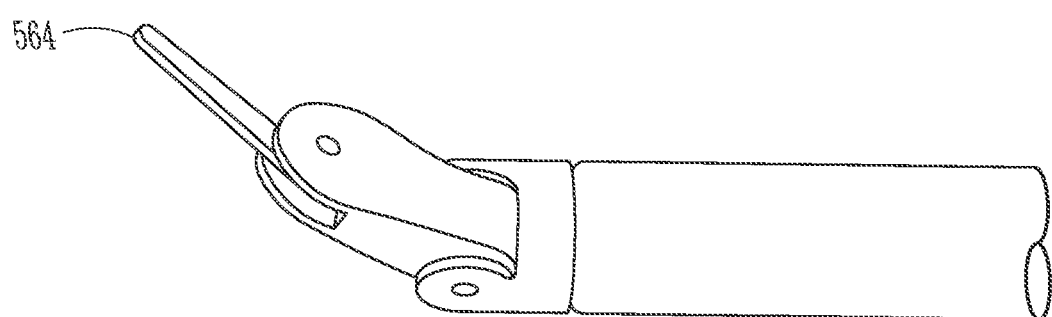
Figure 5H:
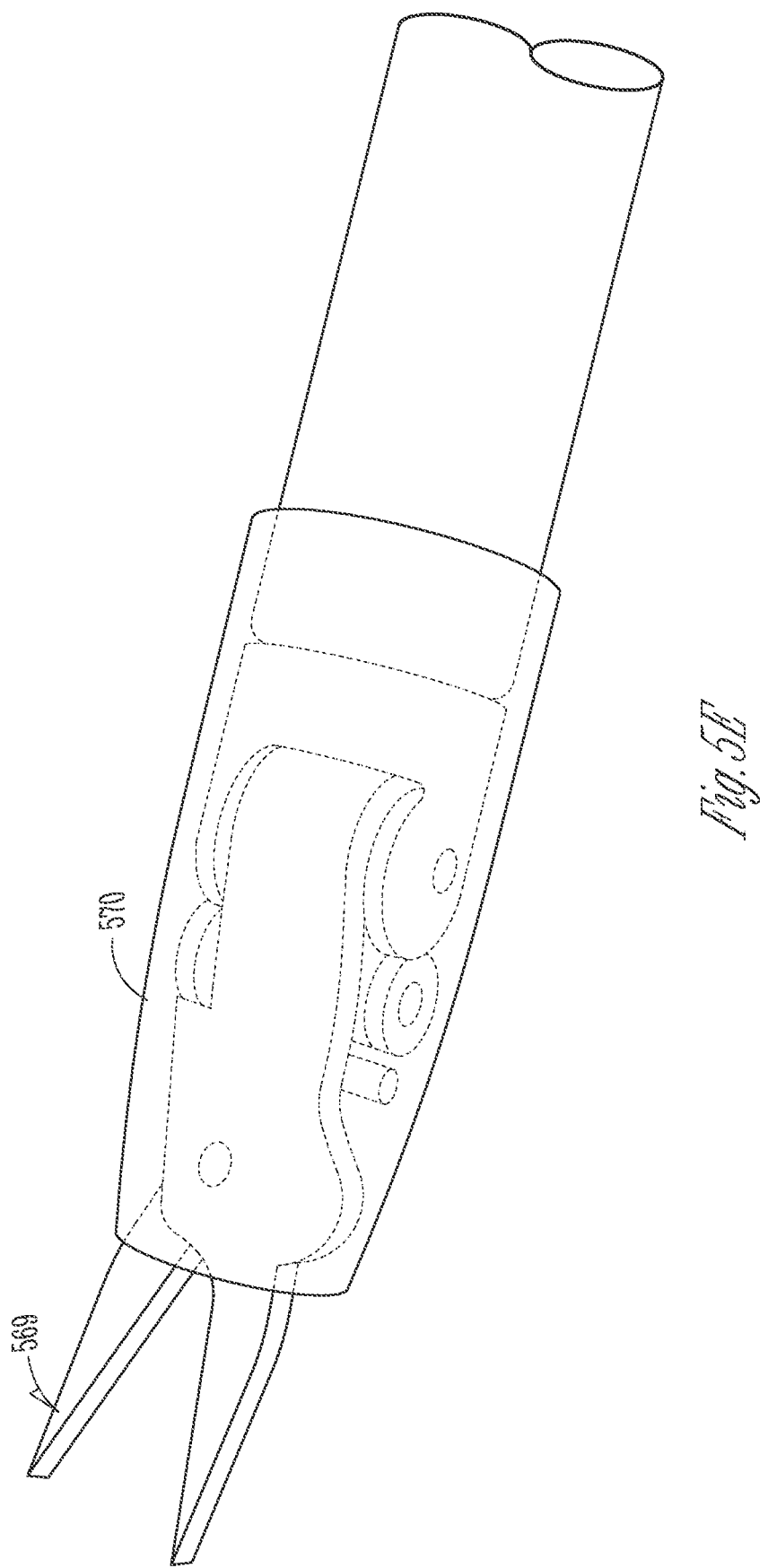

FIGS. 5A-5E, illustrate a variety of alternative robotic tools of differing types and having differing end effectors such as a forceps, graspers, or pliers 561 (FIG. 5A), scissors or cutters 562 (FIG. 5B), etc. Types of end effectors, including the forceps, graspers, or pliers 561, the scissors or cutters 562, DeBakey forceps, microforceps, Potts scissors, and clip appliers include first and second end effector jaws 565, 566, 567, 568 which can pivot relative to each other so as to define a pair of end effector jaws. In some implementations, only one of the end effector jaws is moveable relative to the shaft of the instrument, and the other of the end effector jaws is stationary relative to the shaft of the instrument. In some implementations, both of the end effector jaws are moveable relative to the shaft of the instrument. Other end effectors, including scalpel 563 (FIG. 5C) and electrocautery probe 564 (FIG. 5D) can have a single end effector jaw element. Some end effectors can include additional components such as a cover or a sleeve that, for example, isolates at least a portion of an end effector from the surrounding environment of the manipulation site. For surgical applications, FIG. 5E illustrates generally an example electrocautery scissors 569 that can include a cover 570. In some examples, the scissors 569 can be electrically or thermally energized and the cover 570 can reduce exposure of the scissors 569 to the surrounding surgical environment.

In many embodiments, the tool or its end effector type can be recognized by the system through reading of some or all of the data stored by memory mounted on tool. Information from the memory can be used to perform a number of functions when the tool is loaded on the tool holder of the manipulator arm. For example, the memory can be used to provide a signal verifying that the tool is compatible with the robotic system. The tool memory may store data identifying the tool type to the robotic system so that the robotic system can reconfigure its programming to take full advantage of the tool's specialized capabilities. The tool memory can also store a specific or unique identifier for that particular tool for use in controlling tool life and hence reliability, for determining whether calibration of that particular tool has already been performed during the current (or in some embodiments, a prior) procedure, and the like. Exemplary surgical robotic tool/manipulator interface structures and details regarding data transfer between tools and robotic system processors are more fully described in U.S. Pat. No. 6,331,181 and in an application entitled, "Tool Memory Based Software Upgrades for Robotic Surgery", U.S. patent Ser. No. 10/839,727 hereby incorporated herein in its entirety.

Figure 6:
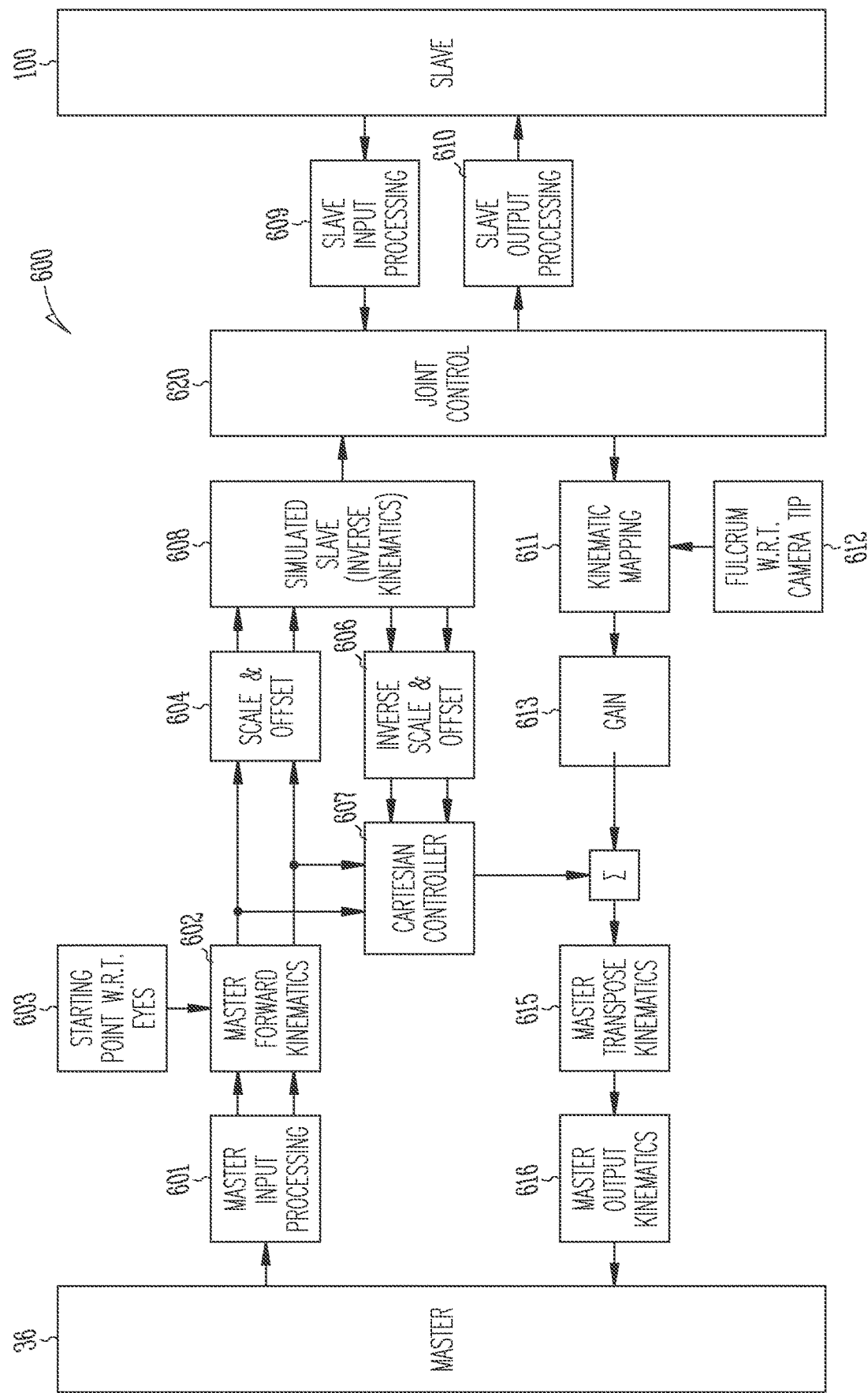
FIG. 6 illustrates generally a block diagram of an example master/slave control system for controlling movement of a slave manipulator of a robotic arm assembly and consequently, the position and orientation of an attached tool, as commanded by movement of a user manipulator by a user.

FIG. 6 illustrates generally a block diagram of an example master/slave control system 600 (also "control logic 600") for controlling movement of a slave manipulator of a robotic manipulation system and consequently, the position and orientation of an attached tool, as commanded by movement of an input device 36 by a user. Both the master and slave manipulators include a number of linkages connected by joints so as to facilitate multiple degrees-of-freedom movement. As the user moves the input device 36 from one position to another during the course of performing a manipulation procedure, sensors associated with the master manipulator joints provide information indicating such command movement in master joint space, and sensors associated with the slave manipulator joints provide information indicating slave manipulator and consequently, tool 26 if the manipulator arm 100 movement in slave joint space for feedback purposes.

A master input processing unit 601 receives the information of the master joint positions, which are sampled at the control system processing rate (e.g., 1300 Hz in the present example), from the master joint sensors in the master manipulator 108, and computes joint velocities from the sensed joint positions. A master forward kinematics processing unit 602 receives the master joint positions and velocities from the master input processing unit 601, transforms them from master joint space to corresponding positions and velocities of the master frame (i.e., the frame associated with the master manipulator 108) in Cartesian space relative to the eye reference frame (i.e., the reference frame associated with the position of the user's eyes), using, for example, a Jacobian matrix and eye related information separately determined and provided in block 603.

A scale and offset processing unit 604 receives the Cartesian position and velocity commands from the master forward kinematics processing unit 602, scales the commanded movement according to a scale factor selected to perform the procedure, and takes into account offsets to generate desired slave tool frame (i.e., the frame associated with the tool 26 of the manipulator arm 100) positions and velocities. The scale adjustment is useful for scaling motion, such that smaller movements of the slave manipulator arm 100 of the robotic arm assembly are desired relative to larger movement of the input device 36 in order to allow more precise movement of the slave tool 56x at an intricate manipulation site. The offsets determine, for example, the corresponding position and/or orientation of an end effector frame (e.g., the frame associated with an end effector of the tool 56x) in the camera reference frame (i.e., the frame associated with the distal tip of the endoscope 140) relative to a position and orientation of the master frame in the eye reference frame.

A simulated slave processing unit 608 receives desired slave tool frame position and velocity commands from the scale and offset processing unit 604, and limits the desired slave tool frame position, orientation and velocities, to assigned Cartesian Limits for instance to enforce correct and intuitive operation of the tool 56x by keeping it within its dexterous workspace. The simulated slave processing unit 608 generates simulated slave joint positions and velocities corresponding to the limited slave tool frame positions and velocities, while making sure that the generated slave joint positions and velocities do not exceed the actual slave joint's range of motion and maximum velocities (i.e., joint limits) even in the vicinity of kinematic singularities for the slave kinematics.

An inverse scale and offset processing unit 606 receives the simulated joint position and velocity commands from the simulated slave processing unit 608, and performs an inverse function to that of the scale and offset processing unit 604 on them. A Cartesian controller 607 receives as first inputs, the inputs to the scale and offset processing unit 604 and as second inputs, the outputs of the inverse scale and offset processing unit 606. The Cartesian controller 607 then generates an error signal as a difference of the first and second inputs, and a Cartesian force from the error signal. For an orientation error, a corresponding torque in Cartesian space is determined.

A master transpose kinematics processing unit 615 receives the Cartesian force FCART through a summation node 614, and generates a corresponding torque in joint space using, for example, the Jacobian transpose matrix and kinematic relationships associated with the input device 36. A master output processing unit 616 receives the master torque signals from the master transpose kinematics processing unit 615, generates electrical currents corresponding to the master torque signals, and supplies the electrical currents to corresponding master joint motors of the master manipulator 108.

As the master input processing unit 601 is receiving master joint positions from sensors in the input device 36, a slave input processing unit 309 is also receiving slave joint positions from position sensors in the slave manipulator at the control system processing rate. A joint control unit 620 receives the slave joint positions from the slave input processing unit 609 and the simulated joint position commands provided from the simulated slave processing unit 608, and generates slave torque command signals for the slave joint motors and master torque feedback command signals for the master joint motors.

The slave torque command signals are generated by the joint control unit 620 so as to drive joints of the slave manipulator until feedback errors calculated in the joint control unit 620 zero out. A slave output processing unit 610 receives the slave torque command signals from the joint control unit 620, converts them into appropriate electrical currents, and supplies the electrical currents to the joint motors of the slave manipulator so as to drive the motors accordingly.

The master torque feedback command signals are generated by the joint control unit 620 as a function of the slave joint position and velocity tracking errors so as to reflect forces being exerted against the tool 56x or its slave manipulator back to the input device 36 so that they may be felt by the user. A kinematic mapping unit 611 receives the master torque feedback command signals from the joint control unit 620, and generates the corresponding Cartesian force at the tip of the tool 56x relative to the camera frame of the endoscope 140 using the slave kinematic configuration and the previously calculated slave fulcrum (e.g., pivot point) position information provided in block 612.

A gain 613 adjusts the magnitude of the Cartesian force so as to ensure system stability while providing adequate force sensation to the user. The gain adjusted Cartesian force is then passed through the summation node 614, and processed along with the Cartesian force provided by the Cartesian controller 607 through the Master transpose kinematics processing unit 615 and Master output processing 616 as previously described in reference to their processing of the Cartesian force provided by the Cartesian controller 607.

Additional details related to conventional aspects of the master/slave control system 600, such as the various reference frames referred to herein and the calculation of the user eye related information provided in block 603 and the slave fulcrum information provided in block 612, which are based upon well-known mathematics, are described, for example, in previously incorporated by reference and commonly owned U.S. Pat. No. 6,424,885, "Camera Referenced Control in a Minimally Invasive Surgical Apparatus."

The joint control unit 620 includes a joint controller for each active joint of the slave manipulator arm 100 of the robotic arm assembly that is being controlled by the master/slave control system 600. In particular, where the slave manipulator arm 100 includes a yaw joint, a pitch joint, and an insertion axis gear, each of these joints or gears will have its own controller, as will each of the drivable mechanical elements for the tool wrist and end effector mechanisms.

As can be understood by reference to FIGS. 1A, 1B, and 6, processor 58 can be configured to effect corresponding movement of a surgical instrument 26 mounted to a robotic manipulator arm 100 in response to movement of an input device 36 by employing software embodying a control logic 600. Control logic 600 can effect movement of an end effector within a manipulation site or an internal surgical site by pivoting an instrument shaft about a point. The control logic 600 employed by processor 58 can generate motor drive signals in response to an input device 36 movement. These motor drive signals are transmitted to the robot arms, and cause movement at the end effector that corresponds to movement at the input device 36. Logic 600 of processor 58 can accommodate a wide variety of differing tool kinematics of a variety of differing tools (such as those illustrated in FIGS. 5A-5G) when information regarding the tool type currently mounted to a robotic arm is made available to the processor.

Maintaining precise control over movement of robotic tools enhances performance. The combination of the manipulation arms and various end-effector and end effector assemblies can be fairly sophisticated and complex mechanical assemblies, particularly where a plurality of end effector elements and/or degrees of freedom are provided at the distal end of the robotic arm. In certain examples, the manipulation arms 100 and end effectors can include drive systems comprising cables, pulleys, rods, gears, and the like, and these mechanical components are subject to both manufacturing tolerances and wear during the life of the tool. Additionally, the manipulator or robotic arm on which the tool is mounted may have a drive system for both transmitting motion to the tool and for moving the tool holder in space, along with having motors and position sensors for receiving drive signals from and transmitting feedback signals to the processor of the robotic system. Many of these components are also subject to deterioration from wear, along with having an initial resolution or tolerance when new. Lastly, coupling of the end effector to the remainder of the instrument or directly to a robotic manipulator will often comprise a mechanical engagement so as to transmit mechanical movement from the motor and drive system of the robotic arm to the end effector, along with structural engagement between the end effector and the remainder of the instrument or the robotic manipulator. Hence, misalignment or improper installation between the end effector can have a number of sources, vary significantly for different end effectors, and have different consequences.

Significant misalignment or installation error between the end effector elements (e.g. of a pair of jaws) and the remainder of the instrument (e.g. an instrument shaft) or a manipulator arm supporting the end effector can be particularly problematic. In some situations, misalignment or mis-installation (incorrect installation) of an effector, or a component of such end effector, can result in inoperable or mis-operating end effectors. In some situations, such misalignment or mis-installation can result less range of motion or motion deviations for the end effector, possibly rendering the end effector useless for a period of time until it can be withdrawn from the manipulation environment and corrected. In some situations, use of a misaligned or mis-installed end effector or component thereof, such as a cover or sleeve, can cause the end effector or component to separate from the remainder of the instrument or a manipulator arm. In some applications, some operations of a manipulation system can be inhibited or completely disabled down until the end effector or its component is correctly installed, or until a separated end effector or component is located and removed from the manipulation site. In some applications, loss of an end effector or component can have the potential to cause damage to an object within the manipulation site. Therefore, in certain examples, the techniques discussed below can help verify correct installation of an end effector or a component thereof, such as before the end effector enters the manipulation site or before certain operations with the end effector is allowed (e.g. operations involving high forces or motions near range of motion limits); and, when an anomaly or an indication of an improperly installed, or incorrectly installed, end effector is determined, an inspection and remedy can be completed before the end effector is allowed to enter the manipulation site or perform particular operations.

Figure 7:
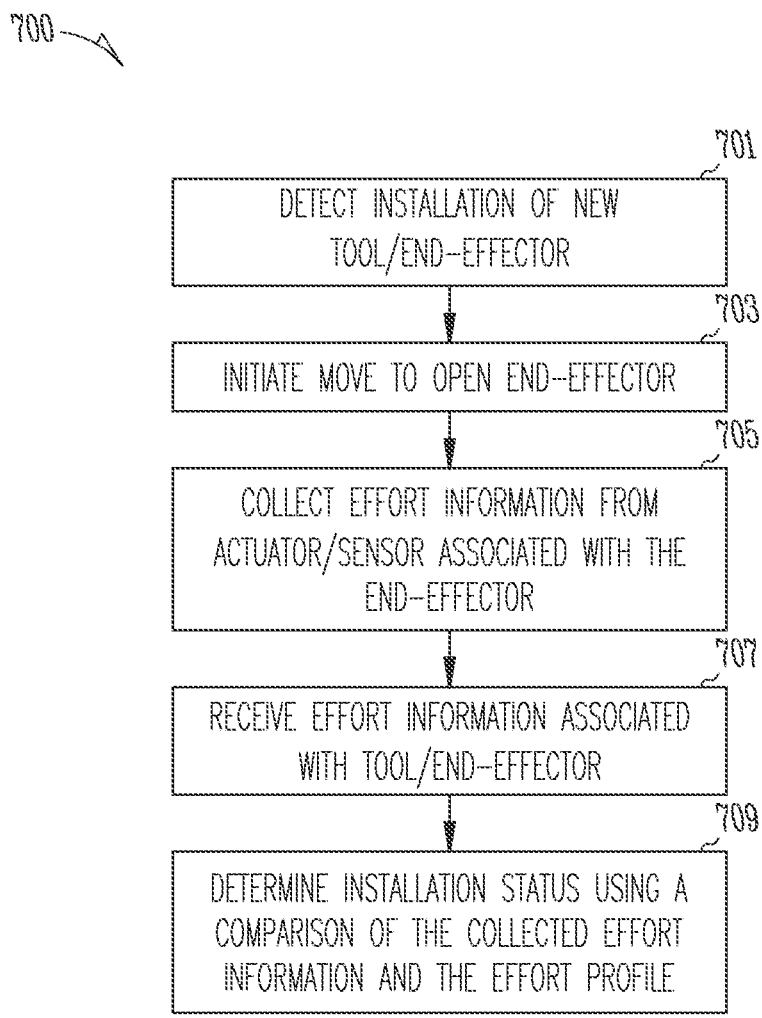
FIG. 7 illustrates generally an example method for detecting an installation status of an end effector or a component of an end effector.

In certain examples, the system can includes instructions that, when executed by the control logic circuitry cause at least a portion of the control logic circuitry and associated actuation and sensing elements to become a diagnostic tool for detecting whether an end effector, or component of the end effector, is properly installed or adjusted. FIG. 7 illustrates generally an example method 700 for detecting an installation status of an end effector or a component of an end effector. At 701, the control logic circuitry can detect an installation of a tool/end effector, for example, by monitoring the tool memory mechanism associated with a robotic arm or manipulation arm of the manipulation system. At 703, the control logic circuitry can initiate a test move of the end effector. In certain examples, performing an "open" test move can include the controller providing a command signal to move a jaw of an end effector to an open-jaw position. In certain examples, the commanded final position of the "open" test move can be to a hard "open" limit of the jaw or jaws, or even to a position a little beyond the hard "open" limit so that the position of actual hard limit can be observed in effort information collected during the "open" test move. At 705, the control logic circuitry can collect effort information such as, but not limited to, any one or any combination of the following: torque applied by the end effector actuator, electrical current used by the end effector actuator, position of the end effector actuator, position of the end effector, force or torque or deflection sensed by one or more end effector force sensors. As the effort information is collected (e.g. as effort information samples collected at discrete points in time or end effector position), or after all of the effort information for a test move is collected, the effort information can be analyzed to detect an installation condition of an end effector or a component thereof.

At 707, the control logic circuitry can receive one or more effort profiles that include one or more types of samples associated with a properly installed end effector or component thereof, an improperly installed end effector or component thereof, or a combination thereof (e.g., a properly installed end effector with an improperly installed cover). The effort profile may be received in any appropriate form. As some examples, the effort profile may include a set of data points indicating effort relative to position, one or more equations modeling the effort relative to position, a set of parameters indicating the expected positions associated with distinct patterns (e.g. knees or other patterns), etc. In certain examples, when the end effector is installed, the control logic circuitry can identify the type of end effector or tool, as discussed above, and can receive additional information such as the one or more effort profiles, such as by using the tool memory. At 709, the control logic circuitry can compare the collected effort information to an effort profile and set a value for the installation status. In certain examples, the initial test motion can open the end effector. In some examples, the control logic circuitry can analyze the collected effort information without receiving an effort profile (or without using a received effort profile), and can optionally provide a failed information status, or installation state, if one or more knees are not detected in the collected effort information. For purposes of the following explanation, an opening motion of an end effector is assumed, but is not limited as such, to correspond to effort information comprising a positive torque or electrical current associated with an actuator controlling the opening or closing of the end effector. In various examples, other types of effort information may be used, including signals from sensors configured to detect end effector forces or torques. Thus, the below techniques may also be used with these other types of effort information.

The control logic can analyze the effort information (e.g. torque or electrical current samples of the initial test move for a significant positive trend (or other significant change) of the torque or electrical current at a particular expected end effector position, or within a particular end effector location window (i.e., range of end effector positions.) In some examples, the end effector position is a function of actuator position, and the torque or electrical current can be compared to the actuator position or within a particular actuator location window (i.e., range of actuator positions)). Thus, for the purposes of the explanation below, the discussion is generally associated with actuator position or actuator location window. However, the below techniques may also be used with other types of information indicative of the end effector position.

In certain examples, the expected actuator position or location window for such significant change can be determined using the effort profile. In certain examples, such a change in torque or electrical current within the expected location window during an opening-type motion can indicate the status that the end effector is properly installed and has reached a fully open position. For end effectors that may include a cover, the actuator location window and whether the significant positive trend started or finished within the location window can indicate whether the cover is properly positioned, installed and improperly positioned, or not installed at all. For example, if the cover is improperly positioned by being placed too distal to the distal end of the end effector, the beginning of the upwardly trending torque or electrical current can occur at actuator positions associated with end effectors that are less open than those associated with the expected actuator position or location window. With some test moves, this upwardly trending torque or electrical current would timewise precede the expected actuator position or location window during the test move. If the cover is installed too proximal relative to the end effector, is a truncated cover, or is not installed at all, the beginning of the upward trending torque or electrical current can occur at actuator positions associated with more open end effectors than those the expected actuator position or location window. With some test moves, this upwardly trending torque or electrical current would timewise fall after the actuator has traversed the expected actuator position or location window during the test move.

Figure 8A:
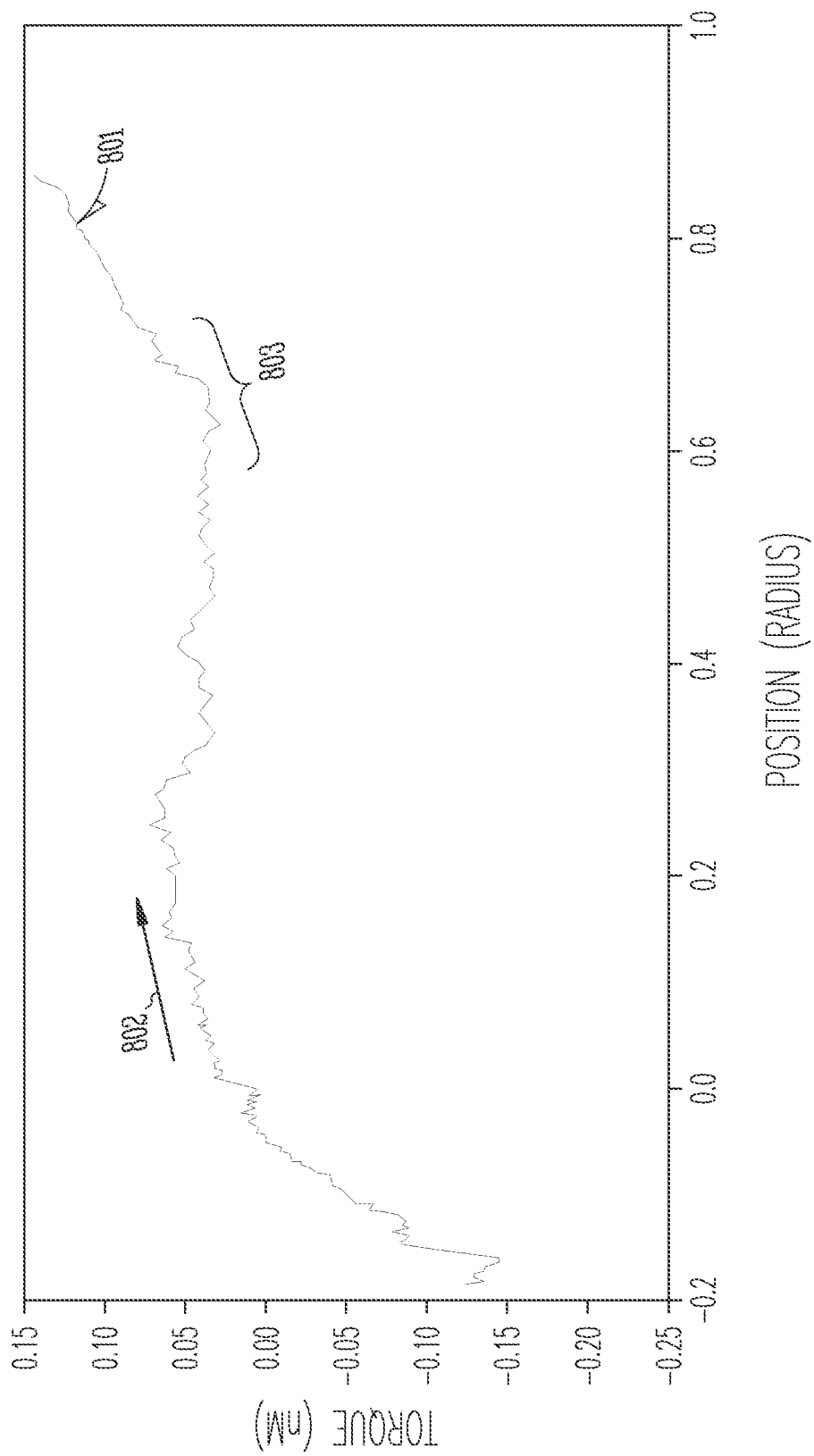
FIGS. 8A and 8B illustrate graphically example effort information collected during an open test move of an end effector that is installed on an axis of a manipulation system.
Figure 8B:
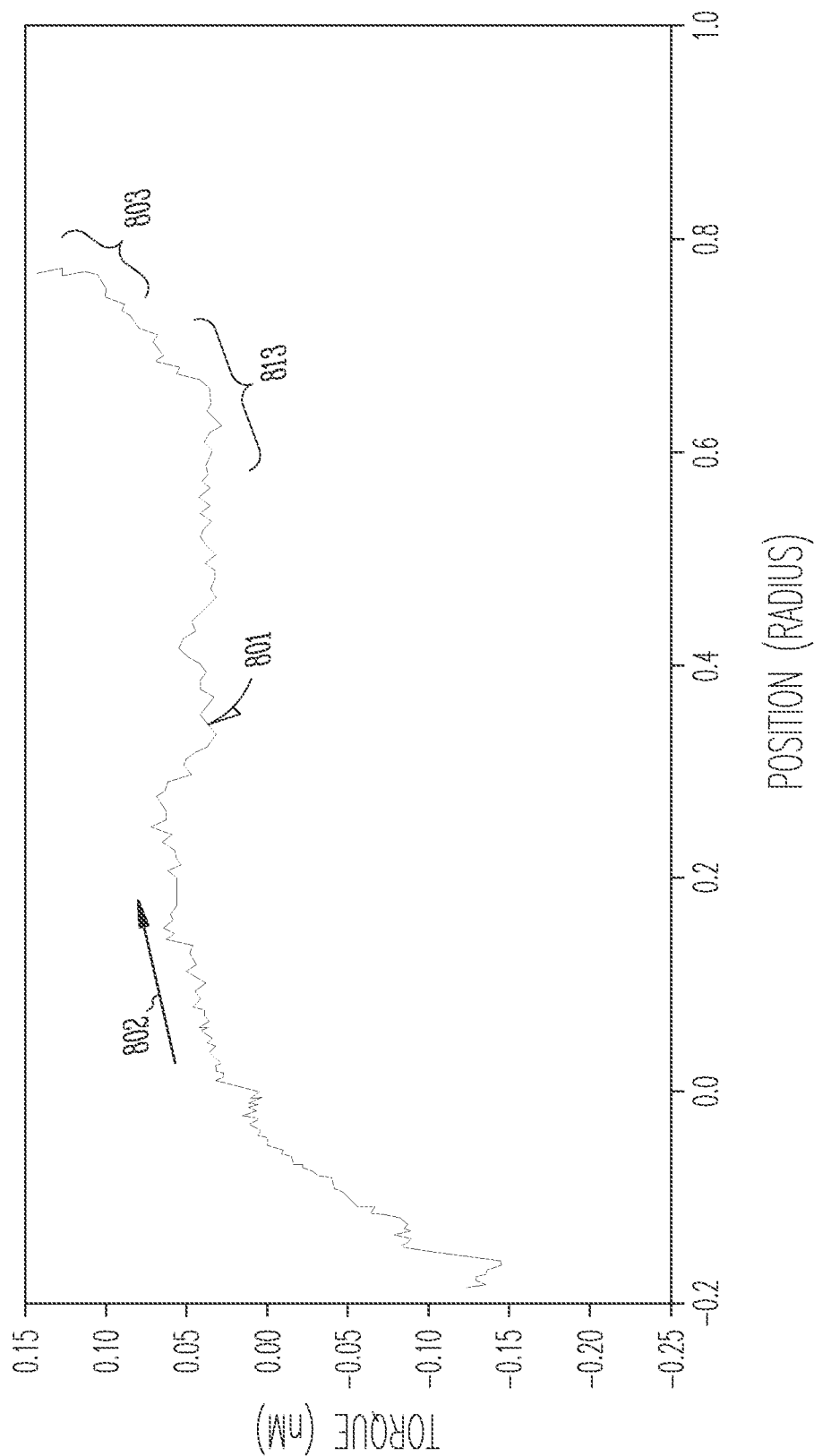

In certain examples, the method can include both an end effector open test move and an end effector close test move. Such a test can provide better resolution of certain installation features as well as the ability to detect more installation features. Installation features can be either expected changes in torque or effort, or unexpected changes in torque or effort during a test move. In certain examples, a knee can be associated with a panned hardware interference, such as a hard limit when a jaw closes, or a detent designed within the range of motion of the jaw movement. FIGS. 8A and 8B illustrate graphically example effort information 801 collected during an open test move of an end effector that is installed on a manipulator arm of a manipulation system. FIGS. 8A and 8B plot the torque output of an actuator of the end effector against the position of either the actuator or the position of the end effector. The arrow 802 shows the timewise collection of the effort information samples in this particular example.

Whether the plot indicates the proper installation of the end effector (or of a component such as the cover) can depend on the type of end effector and one or more effort profiles of a properly installed end effector (or of the cover), one or more effort profiles of an improperly installed end effector (or a component thereof such as the cover), or combination thereof (e.g. a plurality of effort profiles including those for properly and improperly installed end effectors). Effort profiles of an improperly installed end effector can include an effort profile with a combination of properly and improperly installed components; for example, an effort profile of an end effector with a cover may be of an end effector having properly installed jaw components but improperly installed cover.

In the example shown in FIG. 8A, the effort information 801 indicates that as the actuator position moves from 0.6 radians to 0.8 radians, the torque increases to create a distinct pattern of characteristic torque change, or transition, called a "knee" 803 herein. If the shape of the knee 803, and the location of the knee 803 relative to the position of the end effector, or end effector actuator, matches the shape or a corresponding location window of an effort profile of a properly installed end effector or end effector with a cover, the control logic can provide and display an installation status, or installation pass state, reflective of a properly installed end effector, or of a properly installed end effector with a properly installed cover. In certain examples, such a status may release a hardware or a software hold of the manipulation system such that the end effector is allowed to move into a restricted access manipulation environment, such as a surgery environment or an environment around and within a patient.

FIG. 8B illustrates graphically effort information of an end effector with a cover. In contrast to FIG. 8A, the effort information of FIG. 8B shows two "knees" 803, 813 as the open move progresses. The first knee 803 to the furthest right in the plot can be associated with the jaw(s) of the end effector encountering the hard travel limit of the open position of the jaw(s) during the test move. The second knee 813 can be indicative of the jaw(s) encountering or interfacing with the opening of the cover as the jaw(s) open. If the general location of the first and second knees 803, 813 conform to an expected effort profile, the control logic can provide and display an installation status, or installation pass state, reflective of a properly installed end effector with a properly installed cover. If either the first knee 803 or the second knee 813 is missing or is not in an expected location, the control logic can provide and display an installation status reflective of improperly installed end effector or a properly installed end effector with an improperly installed cover. Although FIGS. 8A and 8B discuss effort information associated with a "open" test move, it is understood that the same techniques can be used on effort information collected from a "close" test move, or a combination of effort information collected from both an "open" test" move and a "close" test move, without departing from the scope of the present subject matter.

Figure 9:
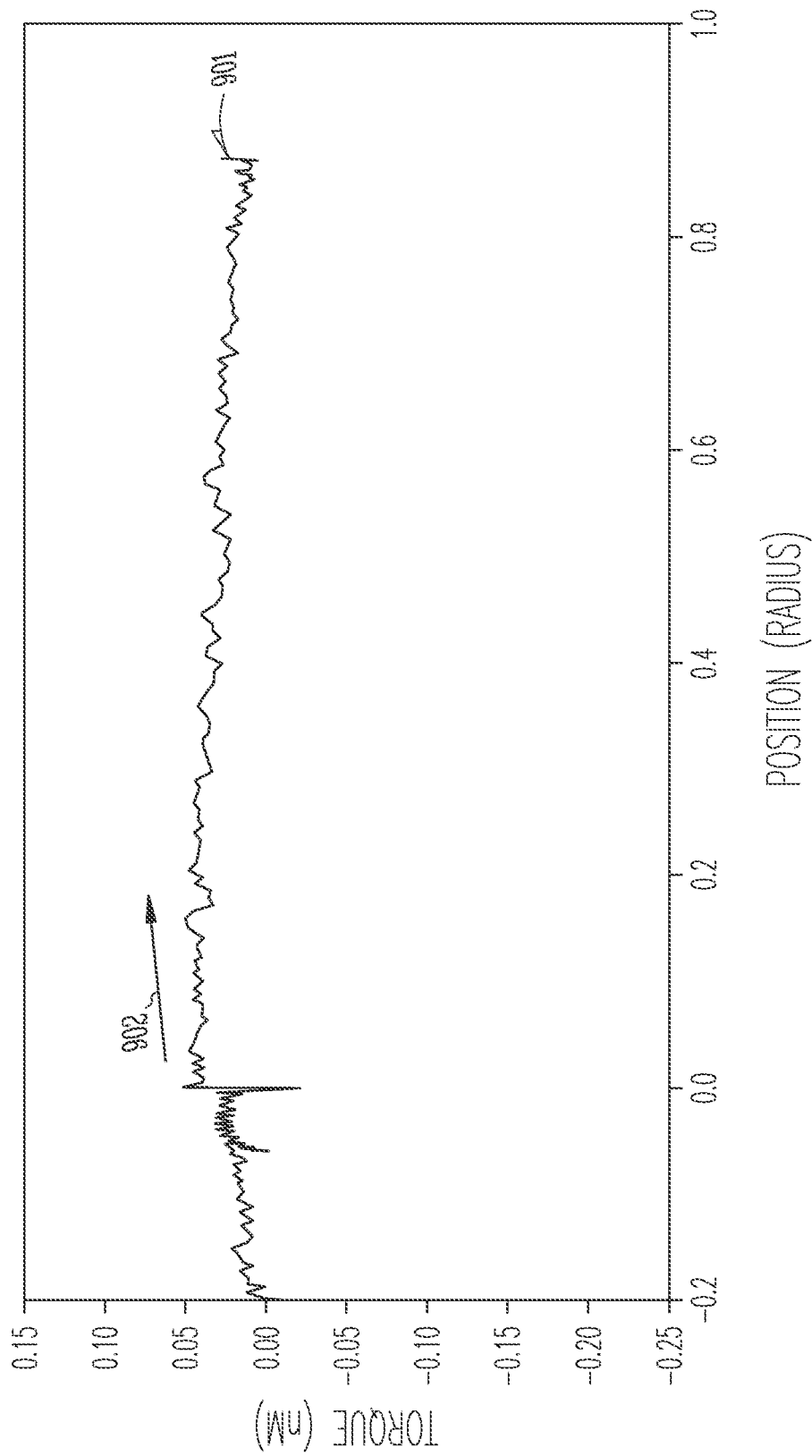
FIG. 9 illustrates graphically example effort information collected during an open test move of an end effector that is improperly installed on an axis of a manipulation system.

FIG. 9 illustrates graphically example effort information 901 collected during an open test move of an end effector that is improperly installed on a manipulator of a manipulation system. FIG. 9 plots the torque output of the actuator against the position of the actuator or position of the end effector. The arrow 902 shows the timewise collection of the effort information samples during this particular test move. For this particular example, a properly installed end effector can show effort samples in the shape of a knee as illustrated in FIG. 8. However, the effort samples of FIG. 9 are relatively constant in magnitude (relatively "flat"), and do not show a distinct pattern of characteristic torque changes like the knee 803. In response, the control logic can provide and display an installation status reflective of an improperly installed end effector (or an improperly installed end effector with an improperly installed cover) at or near the conclusion of this the illustrated test move. In certain examples, such a status can initiate or maintain a hardware hold or a software hold of the manipulation system such that the end effector is not allowed to move into a restricted access manipulation environment, such as a surgery environment or an environment around and within a patient.

Figure 10:
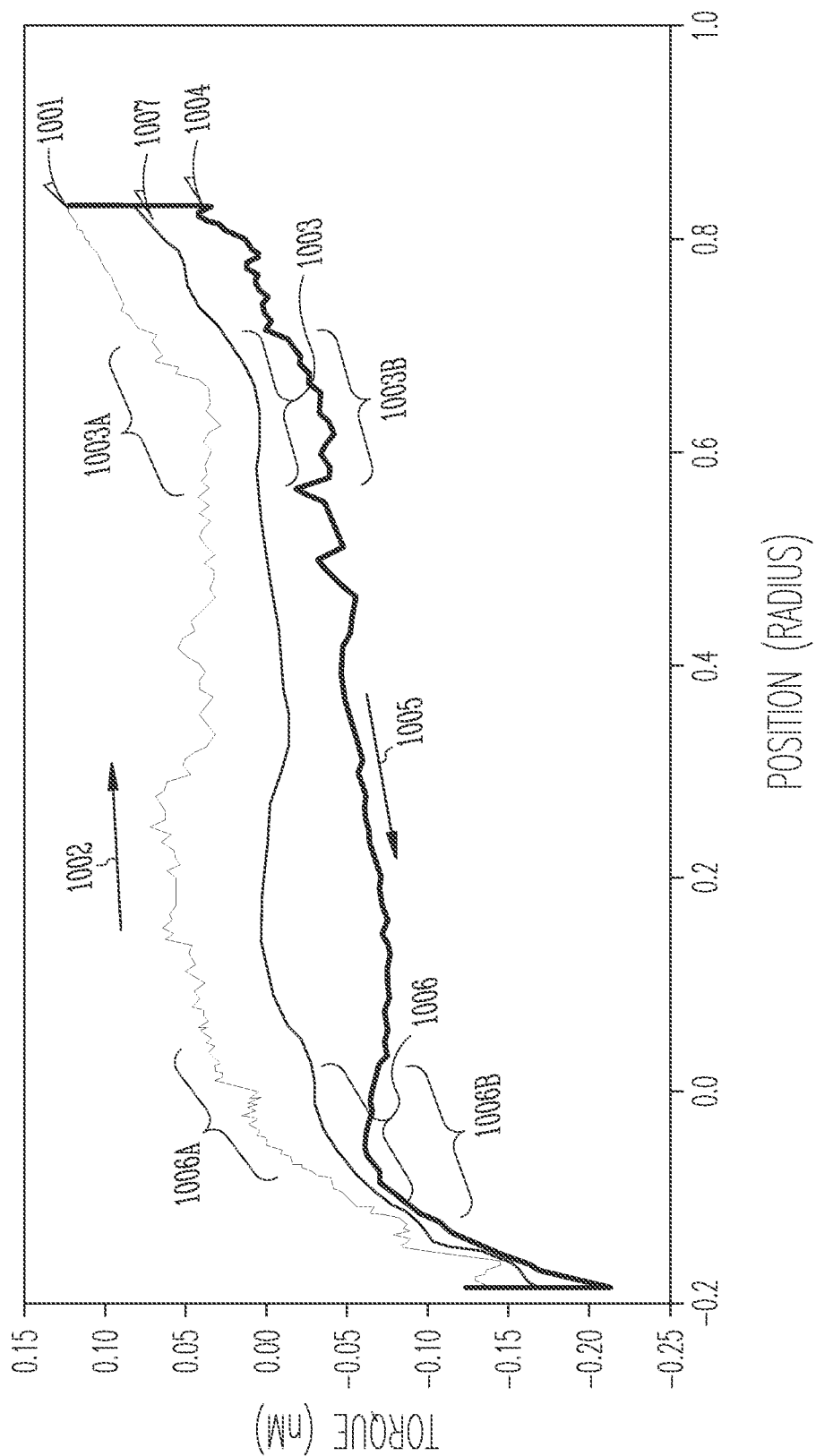
FIG. 10 illustrates graphically an example of effort information collected during an "open" test move and effort information collected during a "close" test move of an end effector that is installed on a manipulation system.

As discussed above, in certain examples, an installation verification test can include more than one test move. FIG. 10 illustrates graphically an example of effort information 1001 collected during an "open" test move and effort information 1004 collected during a "close" test move of an end effector that is installed on a manipulator of a manipulation system. FIG. 10 plots the torque output of the actuator against the position of the actuator. The arrows 1002, 1005 show the timewise collection of the effort samples during these particular test moves. For this particular example, a properly installed end effector can produce effort information samples that form distinctive patterns of characteristic torque changes called "knees" 1003 1003a 1003b, 1006, 1006a, 1006b at or near the travel limits of the properly installed end effector. A first knee 1003, 1003a, 1003b similar to the knee 803 as described with respect to FIG. 8, occurred as the end effector passed into a fully open state during an "open" test move, or passed from a fully open state during a "close" test move. This first knee 1003, 1003a, 1003b can be determined using the effort information of the "open" test move (associated with knee 1003a), or the effort information collected during the "close" test move (associated with knee 1003b). The first knee (associated with knee 1003) can also be determined using the effort information from a combination of the effort information of the "open" and "close" test moves. For example, an average 1007 of samples of the effort information 1001, 1004 between the two test moves can be used. As another example, the knee 1003 can be calculated as an average of the knees 1003a and 1003b.

In a similar fashion, a second knee 1006, 1006a, 1006b can be determined from the effort information collected as the end effector passed into a fully closed position of the jaw(s) during a "close" test move, or passed from a fully closed state during an "open" test move, or from a combination thereof. This second knee 1006, 1006a, 1006b can be determined using the effort information of the "open" test move (this "also associated with knee 1006a), or the effort information collected during the "close" test move (associated with knee 1006b). The second knee (associated with knee 1006) can also be determined using the effort information from a combination of the effort information of the "open" and "close" test moves. For example, an average of samples of the effort information 1001, 1004 between the two test moves can be used. As another example, the second knee 1006 can be calculated as an average of the knees 1006a and 1006b.

In certain examples, the effort information using more than one test move can also give rise to a knee associated with the jaw(s) of an end effector physically interfacing with a cover of the end effector and similar methods as discussed above with reference to knees 1003, 1003a 1003b, 1006, 1006a, 1006b, can be used to identify a knee associated with the cover and the location of that "cover" knee.

It is understood that, upon initial installation of an end effector in some embodiments, a complete "open" test move or complete "close" test move may not be possible in a single continuous move; for example, the initial starting position of the end effector can be in the middle of the travel range of the end effector jaw(s). In some examples, an initial test move can be made to close the jaw(s) of the end effector and to find a "zero" referenced to the "closed" hard limit. After finding the "closed" hard limit and establishing a "zero" position, or reference position of the end effector, the "open" test move can be commenced for detecting an installation status of the end effector. If the "closed" hard lit is not detected during the initial test move, the control logic can provide and display a failed installation status or installation state.

After determining that the first and second knees 1003, 1006 exist in the collected effort information, determining the location of each knee 1003, 1006, and determining other characteristics of the collected effort information, the control logic can compare such determinations with an effort profile and gauge the installation status. Then, the control logic can provide or display an installation status, or installation pass state, reflective of a properly, or correctly, installed end effector, an improperly installed end effector, a properly installed cover, an improperly installed cover, or combinations thereof. This provision or display may be done at or near the conclusion of the one or more test moves. In certain examples, an installation status indicating a properly installed end effector, or of a properly installed end effector and properly installed cover, can release a hardware hold or a software hold of the manipulation system; release of this hold allows the end effector to move into a restricted access manipulation environment, such as a surgery environment. In certain examples, an installation status indicating an improperly installed end effector, or of an improperly installed cover, can initiate or maintain a hardware hold or a software hold of the manipulation system; initiation or maintenance of such a hold may mean that the end effector is not allowed to move into a restricted access manipulation environment or surgery environment.

Figure 11:
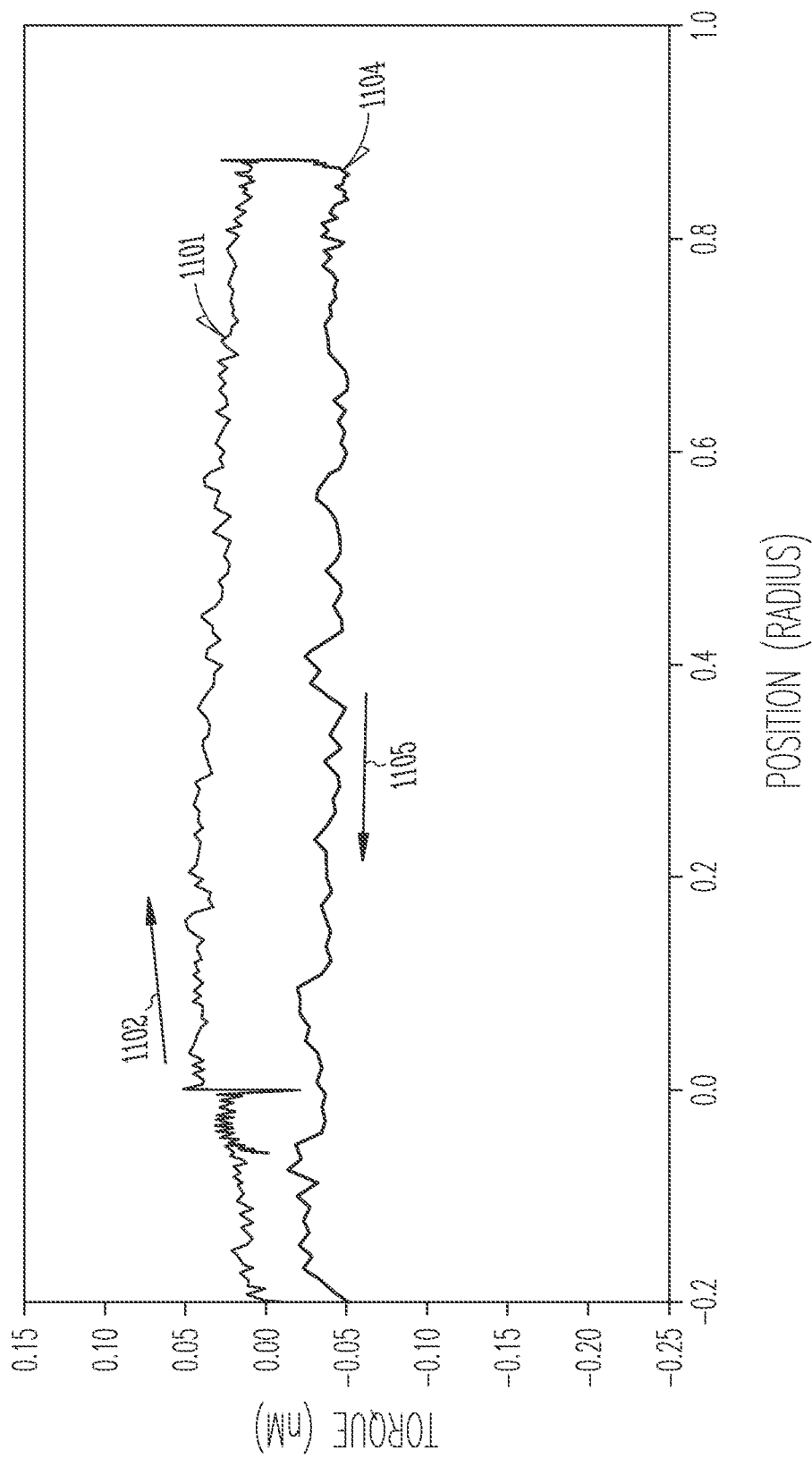
FIG. 11 illustrates graphically example effort information collected during an example test cycle of an end effector that is improperly installed on a manipulation system.

FIG. 11 illustrates graphically example effort information 1101, 1104 collected during a test cycle of an end effector that is improperly installed on a manipulator of a manipulation system. FIG. 11 plots the torque output of the actuator against the position of the actuator. The arrows 1102, 1105 show the timewise collection of the effort samples during a particular test move of the cycle. For this particular example, a properly installed end effector can show effort information samples that, when plotted, show two knees 1003, 1003a 1003b, 1006, 1006a, 1006b as illustrated in FIG. 10. However, the effort information samples of FIG. 11 are relatively constant in magnitude (relatively "flat"), and do not show patterns characteristic of a knee 1003 or 1006. In response, the control logic can provide and display an installation status reflective of an improperly installed end effector, or of an improperly installed end effector with an improperly installed cover. This provision and display may be at or near the conclusion of this the illustrated test move. In certain examples, such a status can initiate or maintain a hardware hold or a software hold of the manipulation system; such a hold may prevent the end effector from moving into a restricted access manipulation environment, such as a surgery environment or an environment around and within a patient.

Various Notes & Examples

Example 1 is a manipulation system comprising: a manipulator arm configured to receive an end effector having a first moveable jaw; a transducer configured to provide effort information of the end effector; and a processor configured to provide a command signal to effect a first test move comprising motion of the first moveable jaw, and to provide an installation status of the of the end effector using first effort information of the first test move, the first effort information indicative of an effort for moving the first moveable jaw via the first test move.

In Example 2, the subject matter of Example 1, wherein the processor is configured to provide a first fail state of the installation status when the processor does not detect a first knee within the first effort information.

In Example 3, the subject matter of Example 2, wherein the processor is configured to provide a second fail state of the installation status when the processor does not detect a second knee within the first effort information.

In Example 4, the subject matter of any of Examples 1-3, wherein the processor is configured to receive an effort profile of a correctly installed end effector, and to compare one or more portions of the effort profile with one or more portions of the first effort information to provide the installation status.

In Example 5, the subject matter of Example 4, wherein the processor is configured to determine a location of a transition associated with a first knee in the first effort information, to execute a comparison of the location with a corresponding location window of the effort profile, and to set the installation status using a result of the comparison.

In Example 6, the subject matter of Example 5, wherein the installation status is set to a second fail state when the location of the transition associated with the first knee in the first effort information is outside the corresponding location window.

In Example 7, the subject matter of any of Examples 5-6, wherein the installation status is set to a first pass state when the location of the transition associated with the first knee in the first effort information is within the corresponding location window.

In Example 8, the subject matter of any of Examples 5-7, wherein the processor is configured to provide a second command signal to effect a second test move comprising second motion of the first moveable jaw, to obtain second effort information of the second test move, and to determine the location of the transition associated with the first knee using an average of the first effort information and the second effort information.

In Example 9, the subject matter of any of Examples 5-8, wherein the processor is configured to determine a second location of a transition associated with a second knee within the first effort information, to execute a second comparison of the second location with a corresponding second location window of the effort profile, and to set the installation status further using a result of the second comparison.

In Example 10, the subject matter of Example 9, wherein the installation status is set to a third fail state if the second location of the transition associated with the second knee is outside the corresponding second location window.

In Example 11, the subject matter of any of Examples 9-10, wherein the installation status is set to a first pass state when the second location of the transition associated with the second knee is within the corresponding second location window.

In Example 12, the subject matter of any of Examples 4-11, wherein the one or more portions of the effort profile includes a corresponding first knee, the corresponding first knee indicative of a properly installed end effector during the first test move.

In Example 13, the subject matter of Example 12, wherein the first test move comprises an opening motion of the first moveable jaw, and wherein the corresponding first knee corresponds to a hard travel limit on opening the first moveable jaw.

In Example 14, the subject matter of any of Examples 12-13, wherein the corresponding first knee corresponds to an engagement of the first moveable jaw with a properly installed cover during the first test move.

In Example 15, the subject matter of any of Examples 12-14, wherein the end effector includes a cover configured to electrically or thermally isolate a portion of the end effector from a surrounding environment, and wherein the one or more portions of the effort profile includes a corresponding second knee, the corresponding second knee corresponding to engagement of the cover by the first moveable jaw during the first test move.

In Example 16, the subject matter of Example 15, wherein the corresponding first knee corresponds to a first amount of opening of the first moveable jaw and the corresponding second knee corresponds to a second amount of opening of the first moveable jaw, and wherein the second amount of opening is smaller than the first amount of opening.

In Example 17, the subject matter of any of Examples 15-16, including the end effector and the cover.

In Example 18, the subject matter of Example 17, wherein the end effector is configured to carry a voltage.

In Example 19, the subject matter of any of Examples 4-18, wherein the processor is configured to receive a second effort profile of an incorrectly installed end effector, and to compare one or more portions of the second effort profile with one or more portions of the first effort information to provide the installation status.

In Example 20, the subject matter of any of Examples 1-19, further comprising a tool supported by the manipulator arm, the tool including the end effector.

In Example 21, the subject matter of any of Examples 1-20, wherein the end effector includes a cover configured to isolate a portion of the end effector from a surrounding environment; and wherein the installation status includes an installation status of the cover.

In Example 22, the subject matter of any of Examples 1-21, wherein the processor is further configured to provide a second command signal to effect a second test move comprising second motion of the first moveable jaw, and to provide the installation status of the of the end effector further using second effort information of the second test move.

In Example 23, the subject matter of Example 22, wherein the first test move comprises opening of the first moveable jaw, wherein the second test move comprises closing of the first moveable jaw, and wherein the processor further establishes a closed position of the first moveable jaw using the second effort information.

In Example 24, the subject matter of any of Examples 1-23, wherein the end effector comprises a second moveable jaw, wherein the first effort information is further indicative of an effort for moving the second moveable jaw.

Example 25 is a method comprising: moving a first moveable jaw of an end effector coupled to a manipulator of a tele-manipulation system during a first test move; receiving first effort information from a transducer, the first effort information associated with moving the first moveable jaw during the first test move; and providing an installation status of the end effector using the first effort information of the first test move.

In Example 25A, the subject matter of Example 25, wherein providing an installation status of the end effector using the first effort information of the first test move includes: detecting if the first effort information includes a first knee; and providing a first fail state of the installation status in response to not detecting a first knee within the first effort information.

In Example 26, the subject matter of Example 26, wherein providing an installation status of the end effector using the first effort information of the first test move further includes: detecting if the first effort information includes a second knee; and providing a second fail state of the installation status in response to not detecting a second knee within the first effort information.

In Example 28, the subject matter of any of Examples 25-27, wherein the providing the installation status includes: receiving an effort profile for a properly installed end effector; and comparing one or more portions of the effort profile with one or more portions of the first effort information to determine the installation status.

In Example 28, the subject matter of Example 28, wherein the providing the installation status further includes: receiving a second effort profile of an incorrectly installed end effector; and comparing one or more portions of the second effort profile with one or more portions of the first effort information to provide the installation status.

In Example 30, the subject matter of any of Examples 25-29, wherein the providing the installation status includes: receiving an effort profile for a properly installed end effector; detecting a first knee in the first effort information; determining the first knee relative to a location of the first moveable jaw during the first test move; comparing the location to a location window of the effort profile; and displaying an installation status of the end effector based on the comparing the location to the location window of the effort profile.

In Example 30, the subject matter of Example 30, wherein the location window corresponds to an expected knee associated with the first moveable jaw interfacing with a cover of the end effector.

In Example 32, the subject matter of any of Examples 30-30, wherein the location window corresponds to an expected knee associated with hardware interference in the end effector.

In Example 33, the subject matter of any of Examples 30-32, wherein the location window corresponds to an expected knee associated with a hard limit, the hard limit associated with the first moveable jaw in a closed position.

In Example 34, the subject matter of any of Examples 30-33, wherein the location window corresponds to an expected knee associated with a hard limit, the hard limit associated with the first moveable jaw in an open position.

In Example 35, the subject matter of any of Examples 30-34, further comprising: providing a second command signal to effect a second test move comprising second motion of the first moveable jaw, obtaining second effort information of the second test move, determining the location using an average of the first effort information and the second effort information.

In Example 36, the subject matter of any of Examples 30-35, wherein the providing the installation status further includes: determining a second location of a transition associated with a second knee within the first effort information, comparing the second location with a corresponding second location window of the effort profile, and displaying the installation status of the end effector further based on the comparing the second location with the corresponding second location window of the effort profile.

In Example 36, the subject matter of any of Examples 25-36, further comprising: providing a second command signal to effect a second test move comprising second motion of the first moveable jaw; and obtaining second effort information of the second test move; and providing the installation status of the of the end effector further using the second effort information of the second test move.

In Example 37, the subject matter of Example 37, wherein the first test move comprises opening of the first moveable jaw, wherein the second test move comprises closing of the first moveable jaw, and wherein the method further comprises: establishing a closed position of the first moveable jaw using the second effort information.

Example 39 is a non-transitory, machine-readable medium, comprising instructions, which when performed by a machine, causes the machine to perform operations to: move a first moveable jaw of an end effector during a first test move; receive first effort information from a transducer, the first effort information associated with moving the first moveable jaw during the first test move; and provide an installation status of the end effector using the first effort information of the first test move.

In Example 39, the subject matter of Example 39, wherein the instructions that causes the machine to provide the installation status of the end effector using the first effort information of the first test move comprises instructions that cause the machine to: detect if the first effort information includes a first knee; and provide a first fail state of the installation status in response to not detecting a first knee within the first effort information.

In Example 41, the subject matter of any of Examples 39-39, wherein the instructions that causes the machine to provide the installation status of the end effector using the first effort information of the first test move comprises instructions that cause the machine to: receive an effort profile for a properly installed end effector; and compare one or more portions of the effort profile with one or more portions of the first effort information to determine the installation status.

In Example 42, the subject matter of any of Examples 39-41, including instructions to cause the machine to perform operations to: move the moveable jaw during a second test move; receive second effort information associated with moving the first moveable jaw during the second test move; average the first effort information and the second effort information to provide average effort information; and determine a location of a first knee relative to a position of the end effector during the first test move using the average effort information.

In Example 42, the subject matter of any of Examples 39-42, further including instructions to cause the machine to perform operations to: provide a second command signal to effect a second test move comprising second motion of the first moveable jaw; and obtain second effort information of the second test move; and provide the installation status of the of the end effector further using the second effort information of the second test move.

Example 44 is at least one machine-readable medium including instructions that, when executed by processing circuitry, cause the processing circuitry to perform operations to implement of any of Examples 1-43.

Example 45 is an apparatus comprising means to implement of any of Examples 1-43.

Example 46 is a system to implement of any of Examples 1-43.

Example 47 is a method to implement of any of Examples 1-43.

Each of these non-limiting examples can stand on its own or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system comprising:
one or more processors, coupled to memory, and in communication with a manipulator arm and a transducer, wherein the manipulator arm is configured to receive installation of an end effector having a moveable jaw, and wherein the transducer is configured to provide effort information of the end effector; and
wherein the one or more processors are configured to:
communicate a signal to the manipulator arm to effect movement of the moveable jaw;
receive, from the transducer, effort information on movement of the moveable jaw;
determine in the effort information a location of a transition associated with movement of the end effector;
compare the location with a corresponding location window of an effort profile; and provide an installation status of the end effector based at least on the comparison.

2. The system of claim 1, wherein the one or more processors are further configured to communicate the signal to effect one of opening or closing the moveable jaw.

3. The system of claim 1, wherein the location window comprises a range of end effector positions.

4. The system of claim 1, wherein the transition comprises a pattern of change in torque.

5. The system of claim 1, wherein the one or more processors are further configured to compare a shape of the transition and the location of the transition to the shape of the transition and corresponding location window of the effort profile.

6. The system of claim 5, wherein the one or more processors are further configured to determine the end effector is properly installed based on the comparison.

7. The system of claim 1, wherein the one or more processors are further configured to compare the location with the corresponding location window of the effort profile of a properly installed end effector.

8. The system of claim 1, wherein the one or more processors are further configured to compare the location with the corresponding location window of the effort profile comprising one or more effort profiles of an improperly installed end effector with one or more of properly or improperly installed components.

9. A method comprising:
communicating, by one or more processors, a signal to a manipulator arm to effect movement of a moveable jaw installed on the end effector;
receive, by the one or more processors, from a transducer effort information on movement of the moveable jaw;
determine, by the one or more processors, in the effort information a location of a transition associated with movement of the end effector;
compare, by the one or more processors, the location with a corresponding location window of an effort profile to determine a status of installation of the end effector; and
provide, by the one or more processors responsive to the comparison, the status of installation of the end effector.

10. The method of claim 9, further comprising communicating, by the one or more processors, the signal to one of open or close the moveable jaw.

11. The method of claim 9, wherein the location window comprises a range of end effector positions.

12. The method of claim 9, wherein the transition comprises a distinct pattern of change in torque.

13. The method of claim 9, wherein the one or more processors are further configured to compare a shape of the transition and the location of the transition to the shape of the transition and corresponding location window of the effort profile.

14. The method of claim 13, further comprising determining, by the one or more processors, the end effector is properly installed based on the comparison.

15. The method of claim 9, further comprising comparing, by the one or more processors, the location with the corresponding location window of the effort profile of an improperly installed end effector.

16. The method of claim 9, further comprising comparing, by the one or more processors the location with the corresponding location window of the effort profile comprising one or more effort profiles of an improperly installed end effort with one or more of properly or improperly installed components.

17. A system comprising:
one or more processors, coupled to memory, and configured to:
receive effort information on opening or closing of a moveable jaw of an end effector being operated responsive to one or more signals from the one or more processors;
identify a shape of a transition at a location in the effort information;
determine a status of installation of the end effector based at least on a comparison of the shape of the transition with one or more shapes of a corresponding location window in one or more effort profiles; and
display the status of installation of the end effector.

18. The system of claim 17, wherein the one or more effort profiles comprises an effort profile of an improperly installed end effector combined with one or more effort profiles of properly or improperly installed components.

19. The system of claim 17, wherein the one or more processors are further configured to identify the location of the transition in the effort information and compare the location to the corresponding location window of the one or more effort profile to determine the status of the installation.

20. The system of claim 17, wherein the one or more processors are further configured to determine the status of installation is that end effector is properly installed based at least on the comparison.

* * * * *